United States Patent
Wang et al.

(10) Patent No.: US 9,840,697 B2
(45) Date of Patent: Dec. 12, 2017

(54) FUSION POLYMERASES

(71) Applicant: Bio-Rad Laboratories, Inc., Hercules, CA (US)

(72) Inventors: Yan Wang, San Francisco, CA (US); Man Cheng, Danville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 103 days.

(21) Appl. No.: 14/562,396

(22) Filed: Dec. 5, 2014

(65) Prior Publication Data

US 2015/0166968 A1 Jun. 18, 2015

Related U.S. Application Data

(60) Provisional application No. 61/912,981, filed on Dec. 6, 2013, provisional application No. 62/006,409, filed on Jun. 2, 2014.

(51) Int. Cl.
*C12N 9/12* (2006.01)
*C12Q 1/68* (2006.01)
*C12N 9/22* (2006.01)

(52) U.S. Cl.
CPC .............. *C12N 9/1252* (2013.01); *C12N 9/22* (2013.01); *C12Q 1/686* (2013.01); *C07K 2319/80* (2013.01)

(58) Field of Classification Search
None
See application file for complete search history.

(56) References Cited

U.S. PATENT DOCUMENTS

| 7,244,602 B2 | 7/2007 | Frey et al. |
|---|---|---|
| 2002/0119461 A1 | 8/2002 | Chatterjee |
| 2003/0138805 A1 | 7/2003 | Loffert et al. |
| 2004/0058362 A1 | 3/2004 | Frey et al. |
| 2008/0227159 A1 | 9/2008 | Hogrefe et al. |
| 2012/0258460 A1 | 10/2012 | Cheng et al. |
| 2012/0329126 A1 | 12/2012 | Wang et al. |

FOREIGN PATENT DOCUMENTS

| WO | 0118213 | 3/2001 |
|---|---|---|
| WO | 0161015 | 8/2001 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
International Search Report and Written Opinion from International Appl. No. PCT/US2014/068887, dated Mar. 30, 2015.
Kaiser et al.; "A comparison of eubacterial and archaeal structure-specific 5'—exonucleases"; *J. Biol. Chem.*; 274:21387-21394 (1999).
Rao et al.; "*Methanococcus jannaschii* flap endonuclease: expression, purification, and substrate requirements"; *J. Bacteriol.*; 180:5406-5412 (1998).
European Patent Application No. EP14867322.1, "Extended European Search Report", dated Sep. 26, 2016, 8 pages.
Holland et al., "Detection of specific polymerase chain readion product by utilizing the 5'-3' exonuclease activity of thermos aquaticus DNA polymerase". Biochemistry. Proceeding ofthe National Academy of Sciences. USA, Washington DC, USA, vol. 88, No. 16, Aug. 1991, pp. 7276-7280.
Wang et al., "A novel strategy to engineer DNA polymerases for enhanced processivity and improved performance in vitro", Nucleic Acids Research, vol. 32, No. 3, Jan. 1, 2004, pp. 1197-1207.
Matsukawa, H. et al.; "A useful strategy to construct DNA polymerases with different properties by using genetic resources from environmental DNA"; *Genes Genet. Syst.*; No. 84; 2009; pp. 3-13.

* cited by examiner

*Primary Examiner* — Richard G Hutson
(74) *Attorney, Agent, or Firm* — Kilpatrick Townsend and Stockton LLP

(57) ABSTRACT

Fusion polypeptides having a heterologous 5'-3' exonuclease domain linked to a polymerase that does not naturally have 5'-3' exonuclease activity, as well as methods of their use are provided. Other aspects are also disclosed.

15 Claims, 4 Drawing Sheets iQ Multiplex Powermix – Taq DNA polymerase based qPCR mix

Negative control – *pfu* based DNA polymerase

Fusion protein #1 – *pfu* based DNA polymerase fused with *pfu* flap endonuclease Fusion protein #2 – fragment of *pfu* based DNA polymerase (USD minus) fused with *pfu* flap endonuclease Fusion protein #3 – *pfu* based DNA polymerase fused with *Da* flap endonuclease Fusion protein #4 – fragment of *pfu* based DNA polymerase (USD minus) fused with *Da* flap endonuclease

FUSION POLYMERASES

CROSS-REFERENCE TO RELATED PATENT APPLICATIONS

The present application claims benefit of priority to U.S. Provisional Patent Application No. 61/912,981, filed Dec. 6, 2013 and U.S. Provisional Patent Application No. 62/006,409, filed Jun. 2, 2014, each of which are incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -1009-2.TXT, created on Jan. 7, 2015, 110,592 bytes, machine format IBM-PC, MS-Windows operating system, is hereby incorporated by reference in its entirety for all purposes.

BACKGROUND OF THE INVENTION

Nucleic acid amplification reactions, such as polymerase chain reaction (PCR), are generally template-dependent reactions in which a desired nucleic acid sequence is amplified by treating separate complementary strands of a target nucleic acid with an excess of two oligonucleotide primers. The primers are extended to form complementary primer extension products which act as templates for synthesizing the desired nucleic acid sequence. In such processes, the nucleic acid sequence between the primers on the respective DNA strands is selectively amplified.

A variety of thermostable polymerases have been discovered that can be used in PCR. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerization and 3' to 5' exonuclease activity.

Taq polymerase has inherent polymerase and 5'-3' exonuclease activity, but does not have 3'-5' exonuclease ("proofreading") activity. Utilizing the inherent 5' to 3' exonuclease activity of Taq, it is possible to achieve PCR amplification and signal release from a target-specific fluorogenic probe (e.g., a "Taqman" probe). The 5' to 3' exonuclease activity of Taq cleaves the 5' terminus of a hybridized oligo probe to release both mono- and oligonucleotides. The probe is hydrolyzed during strand replication so that the accumulating fluorescent signal correlates with amplification.

Pfu DNA polymerase and other family B polymerases has superior thermostability, inhibitor tolerance, and proofreading properties compared to Taq DNA polymerase. Unlike Taq DNA polymerase, Pfu DNA polymerase possesses 3' to 5' exonuclease proofreading activity, meaning that it works its way along the DNA from the 5' end to the 3' end and corrects nucleotide-misincorporation errors. This means that Pfu DNA polymerase-generated PCR fragments will have fewer errors than Taq-generated PCR inserts. However, Pfu and other family B polymerases lack 5'-3' exonuclease activity and thus do not work in probe-based quantitative PCR methods such as those involving Taqman probes.

BRIEF SUMMARY OF THE INVENTION

Provided herein are polypeptides having at least polymerase activity and 5'-3' exonuclease activity, wherein the polypeptides ("fusion polypeptide") comprise a 5'-3' exonuclease domain linked to a heterologous polymerase that does not naturally have 5'-3' exonuclease activity. In some embodiments, the polymerase activity and 5'-3' exonuclease activity are thermostable.

In some embodiments, the heterologous polymerase is a family B polymerase. In some embodiments, the heterologous polymerase is derived from two parental polymerases.

In some embodiments, the 5'-3' exonuclease domain is a flap endonuclease 5'-3' exonuclease domain. In some embodiments, the 5'-3' exonuclease domain is a 5'-3' exonuclease domain from a polymerase.

In some embodiments, the polymerase comprises a uracil-sensing domain (USD). In some embodiments, the USD comprises one or more point mutation substantially eliminating uracil-sensing activity.

In some embodiments, the polymerase lacks at least 10 (e.g., at least 10, 20, 30, 40, 50, 60, 70, 80, 90, 100, 110, 120, or 125) amino acids of a native uracil-sensing domain (USD). In some embodiments, the uracil-sensing domain (USD) is removed or otherwise absent.

In some embodiments, the fusion polypeptide further comprises a heterologous sequence non-specific double-stranded or single-stranded DNA binding domain. In some embodiments, the heterologous sequence non-specific double stranded DNA binding domain comprises a Sso7 DNA binding domain or a Sso7-like DNA binding domain. In some embodiments, the heterologous sequence non-specific double stranded DNA binding domain substantially (e.g., at least 60%) identical to any of SEQ ID NOs: 27, 28, 29, 30, or 31.

In some embodiments, the 5'-3' exonuclease domain and the heterologous family B polymerase are linked by a linker. In some embodiments, the linker is an amino acid linker.

In some embodiments, the carboxyl terminus of the 5'-3' exonuclease domain is linked via a linker to the amino terminus of the family B polymerase. In some embodiments, the amino terminus of the 5'-3' exonuclease domain is linked via a linker to the carboxyl terminus of the family B polymerase.

In some embodiments, the polypeptide has 3'-5' exonuclease activity.

In some embodiments, the polypeptide substantially lacks 3'-5' exonuclease activity. In some embodiments, the polymerase comprises at least one point mutation that substantially eliminates 3'-5' exonuclease activity. In some embodiments, the polymerase comprises a deletion that substantially eliminates 3'-5' exonuclease activity.

In some embodiments, the polypeptide is bound to a reagent that prevents the polymerase activity until the polypeptide is heated.

In some embodiments, the reagent is one or more antibody or aptamer bound to the polymerase.

In some embodiments, the reagent is a reversible covalent chemical modification.

Also provided are kits comprising the fusion polypeptide and other components as described above or elsewhere herein. In some embodiments, the kit further comprises a reverse transcriptase.

Also provided are reaction mixtures, e.g., comprising the fusion polypeptide and other components as described above or elsewhere herein. In some embodiments, the reaction mixture further comprises a polynucleotide primer. In some embodiments, the reaction mixture comprises a sample nucleic acid. In some embodiments, the reaction mixture does not comprise a sample nucleic acid.

In some embodiments, the reaction mixture further comprises a reverse transcriptase.

In some embodiments, the reaction mixture further comprises dUTP and/or a nucleic acid template comprising incorporated uracil.

In some embodiments, the reaction mixture comprises at least one polynucleotide primer and at least one probe with a fluorophore and quencher that is hybridized to a target polynucleotide sequence, wherein during amplification of the target polynucleotide sequence the 5'-3' exonuclease activity releases the fluorophore from the probe, thereby generating fluorescent signal.

Also provided are nucleic acids comprising a polynucleotide encoding the fusion polypeptide as described above or elsewhere herein.

Also provided are methods of performing polymerase chain reaction (PCR) or other type (e.g., isothermal) of amplification. In some embodiments, the method comprises: contacting in an amplification reaction mixture the fusion polypeptide as described herein to a sample comprising nucleic acids under conditions to allow for amplification of a target sequence in the nucleic acids, if present; and detecting the presence or absence of amplified target sequence.

In some embodiments, the amplification reaction comprises at least one polynucleotide primer and at least one probe with a fluorophore and quencher that is hybridized to a target polynucleotide sequence, wherein during amplification of the target polynucleotide sequence the 5'-3' exonuclease activity releases the fluorophore from the probe, thereby generating fluorescent signal.

In some embodiments, the sample comprises one or more inhibitor of PCR. In some embodiments, the sample is crude sample that has not undergone nucleic acid purification. In some embodiments, the sample is blood or serum.

In some embodiments, the amplification reaction comprises dUTP and/or a nucleic acid template comprising incorporated uracil.

In some embodiments, the sample comprises a RNA target nucleic acid and the reaction mixture comprises a reverse transcriptase, and wherein the method further comprises: reverse transcribing the RNA target nucleic acid with the reverse transcriptase to generate a cDNA; and amplifying the cDNA with the polypeptide.

Also provided is a method of making the fusion polypeptide. In some embodiments, the method comprises incubating cells comprising a polynucleotide encoding the polypeptide under conditions to cause expression of the polypeptide in the cells; and purifying the expressed polypeptide.

Also provided are polypeptides having polymerase activity (e.g., thermostable polymerase activity), the polypeptide comprising a family B polymerase but lacking at least 10 amino acids of a native uracil-sensing domain (USD). In some embodiments, the uracil-sensing domain (USD) is absent.

In some embodiments, the polypeptide further comprises a heterologous sequence non-specific double stranded DNA binding domain. In some embodiments, the heterologous sequence non-specific double stranded DNA binding domain comprises a Sso7 DNA binding domain or a Sso7-like DNA binding domain.

Also provided is a kit comprising the polypeptide having polymerase activity (e.g., thermostable polymerase activity), the polypeptide comprising a family B polymerase but lacking at least 10 amino acids of a native uracil-sensing domain (USD).

Also provided are reaction mixtures comprising the polypeptide having polymerase activity (e.g., thermostable polymerase activity), the polypeptide comprising a family B polymerase but lacking at least 10 amino acids of a native uracil-sensing domain (USD).

In some embodiments, the reaction mixture further comprises a polynucleotide primer. In some embodiments, the reaction mixture comprises a sample nucleic acid. In some embodiments, the reaction mixture does not comprise a sample nucleic acid.

In some embodiments, the reaction mixture further comprises a reverse transcriptase.

In some embodiments, the reaction mixture further comprises dUTP and/or a nucleic acid template comprising incorporated uracil.

Also provided are nucleic acids comprising a polynucleotide encoding the polypeptide having polymerase activity (e.g., thermostable polymerase activity), the polypeptide comprising a family B polymerase but lacking at least 10 amino acids of a native uracil-sensing domain (USD).

Also provided are methods of performing polymerase chain reaction (PCR). In some embodiments, the method comprises: contacting in an amplification reaction mixture polypeptide having polymerase activity (e.g., thermostable polymerase activity) to a sample comprising nucleic acids under conditions to allow for amplification of a target sequence in the nucleic acids, if present, wherein the polypeptide comprises a family B polymerase but lacks at least 10, 20, 30, 40, 50, 60, 70, 80, 90, 100, 110, 120, or 125 amino acids of a native uracil-sensing domain (USD); and detecting the presence or absence of amplified target sequence.

In some embodiments, the amplification reaction comprises dUTP and/or a nucleic acid template comprising incorporated uracil.

In some embodiments, the sample comprises a RNA target nucleic acid and the reaction mixture comprises a reverse transcriptase, and wherein the method further comprises: reverse transcribing the RNA target nucleic acid with the reverse transcriptase to generate a cDNA; and amplifying the cDNA with the polypeptide.

Also provided are methods of making the polypeptide. In some embodiments, the method comprises incubating cells comprising a polynucleotide encoding the polypeptide under conditions to cause expression of the polypeptide in the cells; and purifying the expressed polypeptide.

Other aspects of the invention will be evident as described below.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "Sso7" or "Sso7 DNA binding domain" or "Sso7-like DNA binding domain" or "Sso7 domain" refers to nucleic acid and polypeptide polymorphic variants, alleles, mutants, and interspecies homologs that have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:27, 28, 29, 30, or 31. The term includes both full-length Sso7d polypeptides and fragments of the polypeptides that have sequence non-specific double-stranded binding activity. Sso7-like proteins include, but are not limited to, Sso7d, Sac7d and Sac7e.

"Domain" refers to a unit of a protein or protein complex, comprising a polypeptide subsequence, a complete polypeptide sequence, or a plurality of polypeptide sequences where that unit has a defined function.

"Heterologous", when used with reference to portions of a protein, indicates that the protein comprises two or more domains that are not found in the same relationship (e.g., do not occur in the same polypeptide) to each other in nature. Such a protein, e.g., a fusion protein, contains two or more domains from unrelated proteins arranged to make a new functional protein.

"Thermally stable polymerase activity" or "thermostable polymerase activity" of a polypeptide as used herein refers to enzyme activity that catalyzes polynucleotide synthesis by addition of nucleotide units to a nucleotide chain using DNA or RNA as a template and has an optimal activity at a temperature above 45° C., e.g., above 60° C.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "oligonucleotide" or "polynucleotide" or "nucleic acid" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid. Any of the polynucleotides described herein can be included in a vector.

A "DNA polymerase" or a "polymerase," as used herein, refers to an enzyme that performs template-directed synthesis of DNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis, Bacillus stearothermophilus*, and *Thermotoga maritime*, or modified versions thereof. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

BRIEF DESCRIPTION OF THE DRAWINGS

FIG. 1, upper portion: Probe based real-time PCR amplification curves of 100 ng to 100 pg cDNA input using qPCR reagent containing Taq DNA polymerase, which has intrinsic 5'-3' exonuclease activity. Cross labelled traces are no template control (NTC). A standard curve of Cq (signal take-off cycle) against input concentration is shown on the right. PCR efficiency in percentage is shown as E vlaue.

FIG. 1, lower portion: Probe based real-time PCR amplification curves of 100 ng to 100 pg cDNA input using qPCR reagent containing Pfu-based DNA polymerase (a fusion polymerase of Sso7d and pfu/deepVent hybrid DNA polymerase), which lacks intrinsic 5'-3' exonuclease activity. Cross labelled traces are no template control (NTC). A standard curve of Cq (signal take-off cycle) against input concentration is shown on the right. PCR efficiency in percentage is shown as E vlaue.

FIG. 2, upper portion: Probe based real-time PCR amplification curves of 100 ng to 100 pg cDNA input using qPCR reagent containing a fusion DNA polymerase of Pfu flap endonuclease 1 (Pfu FEN1) and Pfu-based DNA polymerase. Cross labelled traces are no template control (NTC). A standard curve of Cq (signal take-off cycle) against input concentration is shown on the right. PCR efficiency in percentage is shown as E vlaue.

FIG. 2, lower portion: Probe based real-time PCR amplification curves of 100 ng to 100 pg cDNA input using qPCR reagent containing a fusion DNA polymerase of Pfu flap endonuclease 1 (Pfu FEN1) and uracil-sensing domain minus Pfu-based DNA polymerase. Cross labelled traces are no template control (NTC). A standard curve of Cq (signal take-off cycle) against input concentration is shown on the right. PCR efficiency in percentage is shown as E vlaue.

FIG. 3, upper portion: Probe based real-time PCR amplification curves of 100 ng to 100 pg cDNA input using qPCR reagent containing a fusion DNA polymerase of Da flap endonuclease 1 (Da FEN1) and Pfu-based DNA polymerase. Cross labelled traces are no template control (NTC). A standard curve of Cq (signal take-off cycle) against input concentration is shown on the right. PCR efficiency in percentage is shown as E vlaue.

FIG. 3, lower portion: Probe based real-time PCR amplification curves of 100 ng to 100 pg cDNA input using qPCR reagent containing a fusion DNA polymerase of Da flap endonuclease 1 (Da FEN1) and uracil-sensing domain minus Pfu-based DNA polymerase. Cross labelled traces are no template control (NTC). A standard curve of Cq (signal take-off cycle) against input concentration is shown on the right. PCR efficiency in percentage is shown as E vlaue.

DETAILED DESCRIPTION OF THE INVENTION

I. Introduction

Figure 1:
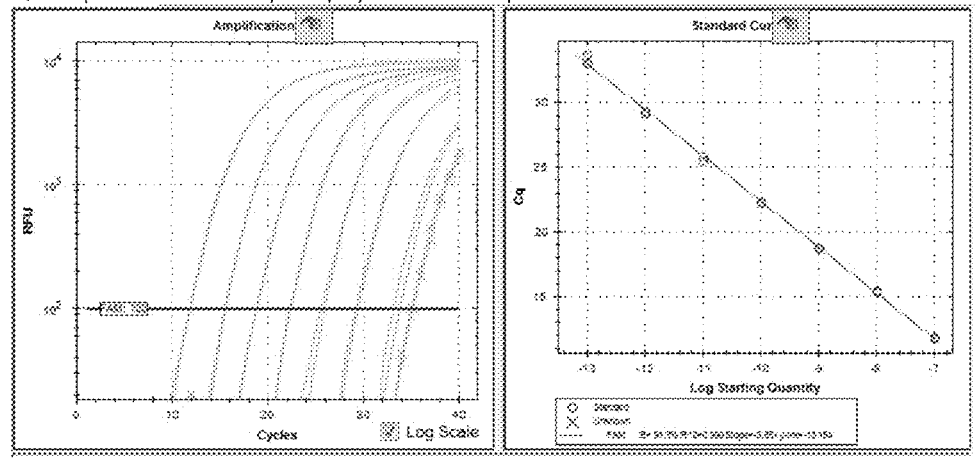
FIG. 1 illustrates results of quantitative detection of probe-based qPCR reactions using two different kinds of control polymerases.
Figure 1:
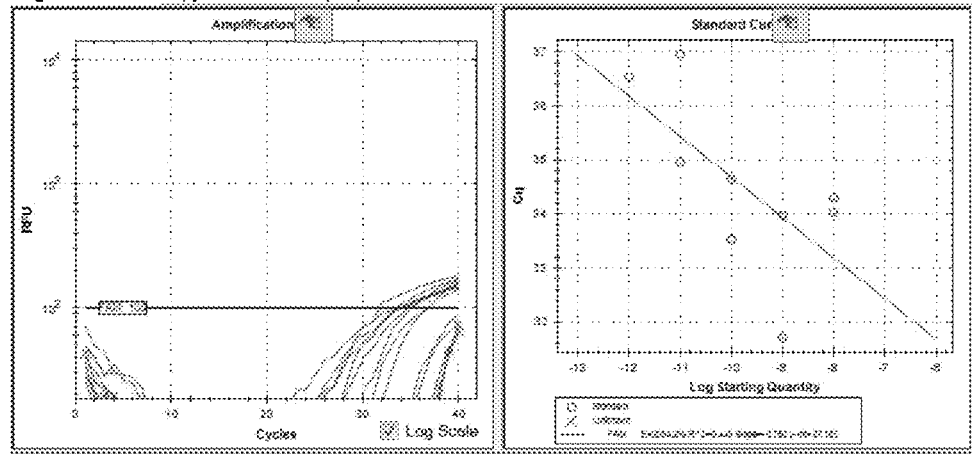
Figure 2:
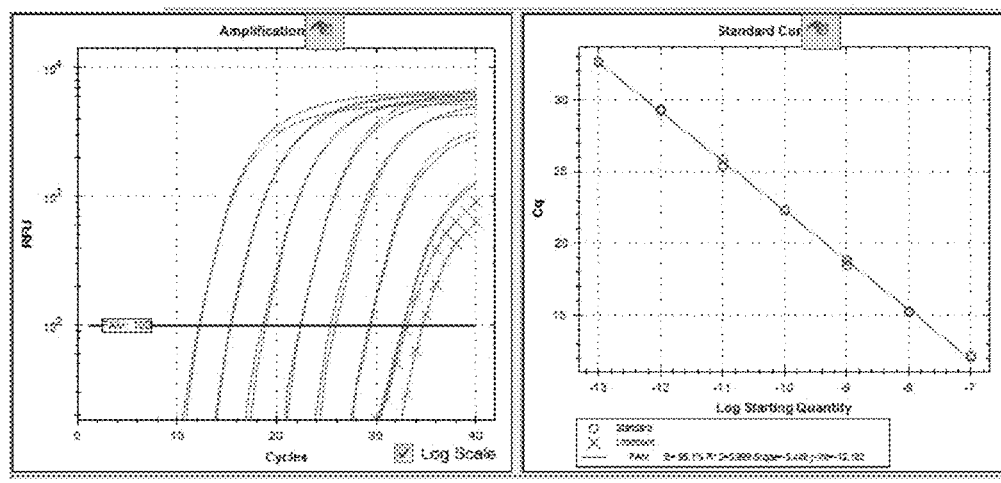
FIG. 2 illustrates results of quantitative detection of probe-based qPCR reactions using Pfu FEN1 5'-3' exonuclease domain fused to DNA polymerase (upper), and Pfu FEN1 5'-3' exonuclease domain fused to DNA polymerase lack of uracil-sensing domain (lower).
Figure 2:
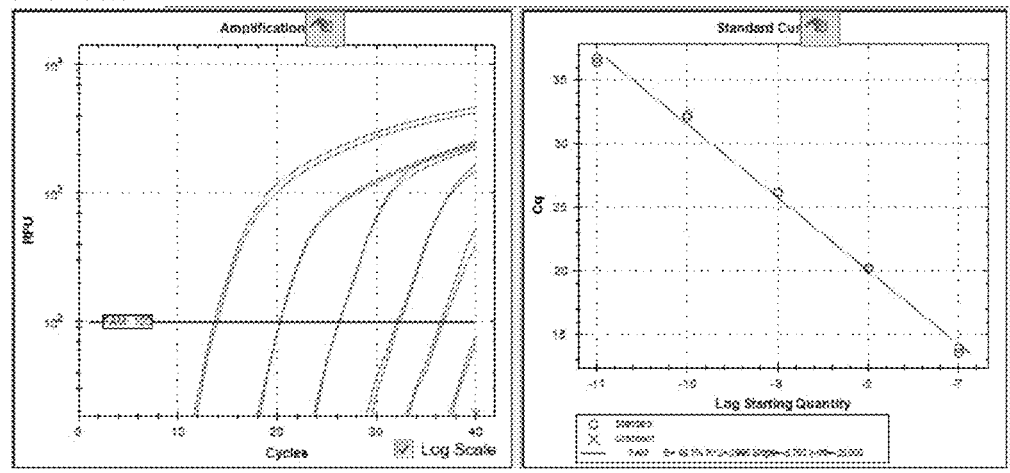

It has been surprisingly discovered that polymerases that do not naturally have a 5'-3' exonuclease activity can be fused with a heterologous 5'-3' exonuclease domain to generate a fusion protein that retains both polymerase and 5'-3' exonuclease activity. This discovery thus allows, for example, for use of family B polymerases and other polymerases that do not naturally have a 5'-3' exonuclease activity in probe-based quantitative PCR (qPCR) applications that rely on a polymerase having 5'-3' exonuclease activity. It is also expected that the fusion protein will retain the improved tolerance of inhibitors of family B polymerases (compared, for example, to the lesser inhibitor tolerance of family A polymerases such as Taq polymerase).

As demonstrated in the examples, 5'-3' exonuclease domains have been fused to the amino terminus of a family B polymerase via a linker and have been shown to have activity in probe-based qPCR methods. Also demonstrated in the example is the generation of a family B polymerase lacking the uracil-sensing domain (USD) and fused to a heterologous 5'-3' exonuclease domain. This demonstrates, for the first time to the inventor's knowledge, that a family B polymerase can retain polymerase activity without the presence (i.e., the structure) of the USD.

II. 5'-3' Exonuclease Domains

It is believed that any domain having 5'-3' exonuclease activity can be fused to a polymerase that does not naturally have a 5'-3' exonuclease activity. Generally, the 5'-3' exonuclease will be fused to the amino terminus of the polymerase, either directly or via a linker. Linkage of the 5'-3' exonuclease and the polymerase can be achieved by any method. A convenient way to link the 5'-3' exonuclease to the polymerase is via recombinant DNA techniques to generate a coding polynucleotide sequence encoding the fused protein and then expressing the protein from the polynucleotide in a cell or via in vitro translation.

A variety of domains having 5'-3' exonuclease activity are known and can be used in the fusion proteins as described herein. In some embodiments, the 5'-3' exonuclease domain is a flap endonuclease (FEN1) or a fragment thereof retaining 5'-3' exonuclease activity. FEN1 proteins are generally from Eukarya and Archea and possess 5'-3' exonuclease activity. A variety of FEN1 proteins (as well as active fragments or variants thereof) are known (see, e.g., Williams, et al., *J. Mol. Biol.* 371(1):34-38 (2007)) and can be used as the 5'-3' exonuclease domain as described herein. In some embodiments the FEN1 protein has thermostable 5'-3' exonuclease activity. Thermostable FEN1 proteins include, but are not limited to, the *Methanococcus jannaschii* FEN1 protein (see, e.g., Rao, et al., *J. Bacteriol.* 180(20):5406-5412 (1998)), the *Pyrococcus furiosus* FEN1 protein (see, e.g., Hosfield, et al., *Cell* 95:135-146 (1998)) or the *Desulfurococcus amylolyticus* FEN1 protein (see, e.g., Mase et al., *Acta Crystallographica Section F* F67:209-213 (2011), as well as active variants (e.g., substantially identical versions thereof) or fragments thereof. An exemplary active FEN1 protein fragment is a FEN1 protein that lacks a PCNA-interacting protein motif (PIP) box. PIP boxes are described in, e.g., Querol-Audi, et al., *Proc. Natl. Acad. Sci USA* 109(22):8528-8533 (2012). Exemplary thermostable FEN1 protein sequences include those substantially identical to SEQ ID NOs: 10 or 24.

In some embodiments, the 5'-3' exonuclease domain is from a heterologous polymerase. For example family A polymerases have 5'-3' activity and thus fragments of a family A polymerase can be used as the 5'-3' exonuclease domain. Conserved sites within the 5'-3' exonuclease domain of the *E. coli* polymerase (Pol I) has been described. See, e.g., Gutman et al., *Nucleic Acids Res.* 21(18):4406-7 (1993). The 5'-3' exonuclease domain of various thermostable polymerases have also been identified and separately expressed with retained activity. See, e.g., Choi et al., *Biotechnol. Letts.* 23:1647-52 (2001) and Kaiser et al., *J. Chem. Biol.* 274(30):21387-21394 (1999). An exemplary listing of sources of 5'-3' exonuclease domains useful in the protein fusions described herein include, but are not limited to, *Thermus thermophilus* (Tth) DNA polymerase, *Thermus aquaticus* (Taq) DNA polymerase, *Thermotoga neopolitana* (Tne) DNA polymerase, *Bacillus stearothermophilus* DNA polymerase, and *Thermotoga maritima* (Tma) DNA polymerase, and mutants, and variants (e.g., substantially identical versions thereof) and derivatives thereof. An exemplary Taq 5'-3' exonuclease domain is SEQ ID NO:35, or a substantially identical amino acid sequence thereof.

In some embodiments, the coding sequences of each polypeptide in a resulting fusion protein (e.g., the 5'-3' exonuclease domain and the polymerase and optionally the sequence non-specific DNA binding protein discussed further below) are directly joined at their amino- or carboxy-terminus via a peptide bond. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) *Gene* 40:39-46; Murphy et al. (1986) *Proc. Natl. Acad. Sci. USA* 83:8258-8262; U.S. Pat. Nos. 4,935,233 and 4,751,180, each of which is hereby incorporated by reference in its entirety for all purposes and in particular for all teachings related to linkers. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference. In some embodiments, linker sequences of use in the present invention comprise an amino acid sequence according to SEQ ID NO: 12 or 21.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining a DNA binding domain and polymerase domain include ionic binding by expressing negative and positive tails and indirect binding through antibodies and streptavidin-biotin interactions. See, e.g., Bioconjugate Techniques, Hermanson, Ed., Academic Press (1996).

As previously described, nucleic acids encoding the polymerase or DNA binding domains can be obtained using routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117, each of which is incorporated by reference in its entirety for all purposes and in particular for all teachings related to amplification methods.

Modifications can additionally be made to the 5'-3' exonuclease domain (or the polymerase) without diminishing their biological activity. Some modifications may be made to facilitate the cloning, expression, or incorporation of a domain into a fusion protein. Such modifications can include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The fusion polypeptides described herein can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (Bioprocess Technology, Vol. 22), Marcel Dekker, 1994.

There are many expression systems for producing the fusion polypeptides described herein that are known to those of ordinary skill in the art. See, e.g., *Gene Expression Systems*, Fernandex and Hoeffler, Eds. Academic Press, 1999; Sambrook and Russell, supra; and Ausubel et al, supra.) Typically, the polynucleotide that encodes the fusion polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived PL promoter and N-gene ribosome binding site (Shimatake et al., *Nature* (1981) 292: 128). The particular promoter system is not critical, any available promoter that functions in prokaryotes can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HA-tag, 6-His (SEQ ID NO:39) tag, maltose binding protein, VSV-G tag, anti-DYKDDDDK (SEQ ID NO:40) tag, or any such tag, a large number of which are well known to those of skill in the art.

III. Polymerases

As noted above, it is believed that any polymerase not naturally having 5'-3' exonuclease activity can be used as described herein as a fusion partner with a heterologous 5'-3' exonuclease domain. Exemplary polymerases not naturally having 5'-3' exonuclease activity include family B polymerases. In some embodiments, the family B polymerase is an archeal family B polymerase.

A number of DNA polymerases have been grouped under the designation of DNA polymerase family B. Six regions of similarity (numbered from I to VI) are found in all or a subset of the B family polymerases. The most conserved region (I) includes a conserved tetrapeptide with two aspartate residues. Its function is not yet known. However, it has been suggested that it may be involved in binding a magnesium ion. All naturally-occurring polymerase sequences in the B family contain a characteristic DTDS (SEQ ID NO:41) motif, and possess many functional domains, including a 5'-3' elongation domain, a 3'-5' exonuclease domain, a DNA binding domain, and binding domains for both dNTP's and pyrophosphate (see, e.g., Zhou M, et al., *Acta Crystallographica*. Section D, Biological Crystallography 54(Pt 5):994-995 (1998)). Conserved amino acid residues of family B polymerases are described, for example, Hopfner, K.-P., et al., *Proc. Natl. Acad. Sci USA* 96: 36003605 (1999) in general and in FIG. 3 in particular.

Exemplary polymerases useful in the fusions described herein include, but are not limited to, *Pyrococcus horikoshii* (e.g., accession number O59610), *P. abyssi* (e.g., accession number P77916), *P. glycovorans* (e.g., accession number CAC12849), *Pyrococcus* sp. GE23 (e.g., accession number CAA90887), *Pyrococcus* sp. GB-D (e.g., accession number Q51334), *P. furiosus* (e.g., accession number P61875), *P. woesei* (e.g., accession number P61876), *Thermococcus kodakaraensis* (e.g., accession number P77933), *T. gorgo-*

*narius* (e.g., accession number P56689), *T. fumicolans* (e.g., accession number P74918), T. sp. 9oN-7 (e.g., accession number Q56366), *T. onnurineus* NA1 (e.g., accession number ABC11972), *T. litoralis* (e.g., accession number P30317), and *T. aggregans* (e.g., accession number O33845), as well as fragments and variants (e.g., substantially identical versions thereof) thereof that retain polymerase activity. In some embodiments, the polymerase is derived from two parental polymerases, e.g., Pfu and DeepVent. Such polymerases are described for example in U.S. Application Publication Nos. 20040219558; 20040214194; 20040191825; 20030162173, each of which is hereby incorporated by reference in its entirety for all purposes and in particular for all teachings related to hybrid polymerases.

In some aspects, the fusion polypeptide has 3'-5' exonuclease activity and an active uracil sensing activity, as well as polymerase activity. In other aspects, the polymerase lacks one or more 3'-5' exonuclease activity and an active uracil sensing activity. As described in more detail below, in some aspects, the polymerase lacks or substantially lacks the uracil sensing domain (USD).

In one aspect, the fusion polypeptide lacks 3'-5' exonuclease activity. In one embodiment, such fusion polypeptides comprise a double point mutation in the polymerase domain that provides this exonuclease deficiency. A variety of mutations can be introduced into a native or mutant polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17 (1991) and Derbyshire et al., *Methods in Enzymology* 262: 363 85 (1995). It will be understood that while the above-described mutations were originally identified in one polymerase, one can generally introduce such mutations into other polymerases to reduce or eliminate exonuclease activity. In a specific embodiment, a polymerase comprises the double point mutation corresponding to D141A/E143A in the polymerase domain. Sequence comparisons can be performed using any BLAST including BLAST 2.2 algorithm with default parameters, described in Altschul et al., *Nuc. Acids Res.* 25:3389 3402 (1977) and Altschul et al., *J. Mol. Biol.* 215:403 410 (1990), respectively, to determine the "corresponding" amino acid in a different polymerase.

Figure 3:
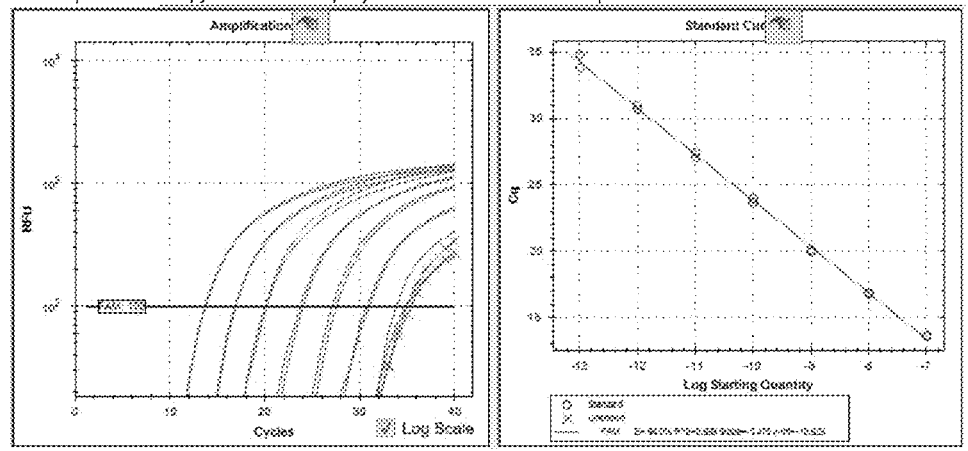
FIG. 3 illustrates results of quantitative detection of probe-based qPCR reactions using Da FEN1 5'-3' exonuclease domain fused to DNA polymerase (upper), and Da FEN1 5'-3' exonuclease domain fused to DNA polymerase lack of uracil-sensing domain (lower).
Figure 3:
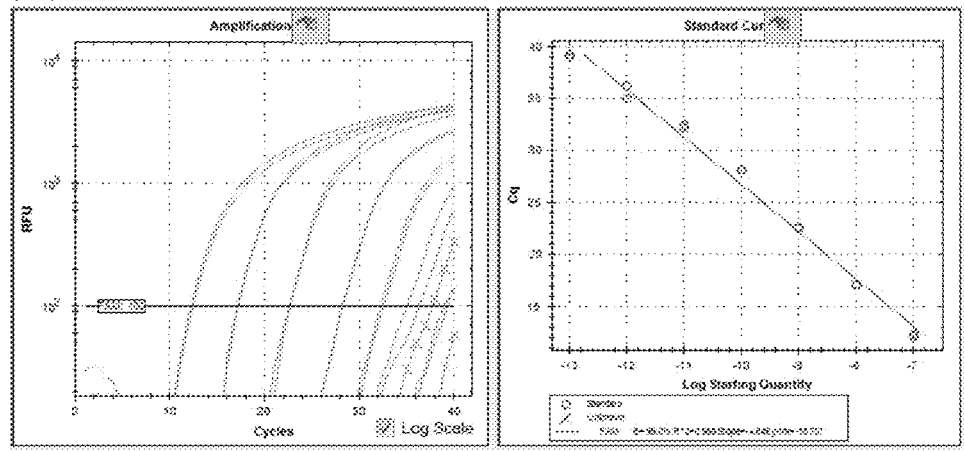

In one aspect, the polymerase in the fusion polypeptide lacks a uracil sensing domain (USD). The USD is generally described in Kim et al., *J. Microbiol. Biotechnol.* 18(8): 1377-1385 (2008), which also describes assays for measuring uracil sensing. FIG. 3 of Kim et al, supra, provides an alignment of various USDs. USDs are also described in, e.g., European Patent Application Publication No. EP1463809B1. As described in the Examples below, it has been surprisingly discovered the entire USD can be removed from a family B polymerase without significantly affecting polymerase activity. Accordingly, in some embodiments, the fusion polypeptides as described herein lack at least a portion (e.g., at least 10, 20, 30, 40, 50, 60, 70, 80, 90, 100, 110, 120, or 125 contiguous amino acids), a majority of, or all of the native USD. The USD of an exemplary Pfu/DeepVent hybrid DNA polymerase (SEQ ID NO: 20) is ILDADYITEEGKPVIRLFKKENGEFKIEHDRTFRPYI-YALLKDDSKIEEVKKITAERHGKIV RIVDAEKVEK-KFLGRPITVWRLYFEHPQDVPTIREKIREHSAV-VDIFEYDIPFAKRY (SEQ ID NO:25) and the USD of Pfu is ILDVDYITEEGKPVIRLFKKENGKFKIEHDRT-FRPYIYALLRDDSKIEEVKKITGERHGKIV RIVDVEK-VEKKFLGKPITVWKLYLEHPQDVPTIREKVREHPAV-VDIFEYDIPFAKRY (SEQ ID NO:38), though it will be appreciated that USDs of other polymerases may vary at least somewhat in sequence from SEQ ID NO:25 (e.g., a USD can be substantially identical to SEQ ID NO:25). As shown in the Examples, the inventors have found that additional amino acids (e.g., corresponding to SEQ ID NO:26) following the USD can also be conveniently removed from the polymerase without significantly affecting polymerase activity. Removal or inactivation of the USD can be useful to enable the fusion polypeptide to amplify templates comprising incorporated uracils, deaminated bases (e.g., inosine), and/or bisulfite-converted bases, for example.

IV. Sequence Non-Specific DNA Binding Domains

In some embodiments, fusion polypeptides described herein comprise a heterologous DNA binding domain. A DNA binding domain is a protein, or a defined region of a protein, that binds to nucleic acid in a sequence-independent matter, e.g., binding does not exhibit a gross preference for a particular sequence. DNA binding domains may bind single or double stranded nucleic acids.

The DNA binding proteins of use are generally thermostable. Examples of such proteins include, but are not limited to, the Archaeal small basic DNA binding proteins Sso7d and Sso7d-like proteins (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998), Archaeal HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell*:99, 155-166, 1999; De Felice et al., *J. Molec. Biol.* 291, 47-57, 1999; and Zhang et al., *Biochemistry* 34:10703-10712, 1995).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, *Biochemistry* 34:10063-10077, 1995; Gao et al., *Nat. Struct. Biol.* 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. A variety of mutations in the Sso7 binding domain have been described in, e.g., US Patent Application Nos. 2005/0048530; 2007/0141591; and WO 2012/138417.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a).

Certain helix-hairpin-helix motifs have been shown to bind DNA nonspecifically and enhance the processivity of a DNA polymerase to which it is fused (Pavlov et al., *Proc Natl Acad Sci USA*. 99:13510-5, 2002). Single-stranded DNA binding proteins have also been described.

Additional DNA binding domains suitable for use can be identified by homology with known DNA binding proteins and/or by antibody cross reactivity, or may be found by means of a biochemical assay. DNA binding domains may be synthesized or isolated using the techniques described herein and known in the art.

Sequence non-specific single-stranded or doubled-stranded nucleic acid binding domains for use can also be identified by cross-reactivity using antibodies, including but not limited to, polyclonal antibodies that bind to known nucleic acid binding domains. Polyclonal antibodies are generated using methods well known to those of ordinary skill in the art (see, e.g., Coligan, *Current Protocols in Immunology* (1991); Harlow & Lane, *Antibodies, A Laboratory Manual* (1988)). Those proteins that are immunologically cross-reactive binding proteins can then be detected by a variety of assay methods. For descriptions of various formats and conditions that can be used, see, e.g., Methods in Cell Biology: Antibodies in Cell Biology, volume 37 (Asai, ed. 1993), Coligan, supra, and Harlow & Lane, supra.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radiolabeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabeled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain binds to double-stranded nucleic acids in a sequence-independent fashion, i.e., a binding domain of the invention binds double-stranded nucleic acids with a significant affinity, but, there is no known double-stranded nucleic acid that binds to the domain with more than 100-fold more affinity than another double stranded nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific single-stranded or double-stranded nucleic acid binding domains can also be assessed, for example, by assaying the ability of the single-stranded or double-stranded binding domain to increase processivity or efficiency of a modifying enzyme or, in the case of double-stranded nucleic acid binding domains, to increase the stability of a nucleic acid duplex by at least 1° C. can be determined.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_m$ of the double-stranded substrate can be determined from the midpoint of the melting curve. The effect of the sequence-non-specific double-stranded nucleic-acid-binding protein on the $T_m$ can then be determined by comparing the $T_m$ obtained in the presence of the modified enzyme with that in the presence of the unmodified enzyme. (The protein does not significantly contribute to the UV absorbance because it has a much lower extinction coefficient at 260 nm than DNA). A domain that increases the $T_m$ by 1° C., often by 5° C., 10° C. or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

In some embodiments, the fusion polypeptides described herein comprise an Sso7 polypeptide sequence that is substantially identical to SEQ ID NOs: 27, 28, 29, 30, or 31. In some embodiments, the Sso7 polypeptide sequence has amino acid substitutions compared to the native (wildtype) Sso7d sequence. In some embodiments, the amino acid substitutions include amino acid changes from the native amino acid at the positions corresponding to K28 and/or R43 of SEQ ID NO:27. It should be understood that such position designations do not indicate the number of amino acids in the claimed molecule per se, but indicate where in the claimed molecule the residue occurs when the claimed molecule sequence is maximally aligned with SEQ ID NO:27.

Any Sso7 DNA binding protein domain can be substituted at the K28 and/or R43 position corresponding to SEQ ID NO:27. Thus, for example, in some embodiments, the variant Sso7 polypeptide sequence is substantially (e.g., at least 60, 70, 80, 85, 90, or 95%) identical to any of, e.g., SEQ ID NOS:27, 28, 29, 30, or 31, and comprises an amino acid other than K at the amino acid position corresponding to K28. In some embodiments, the amino acid position corresponding to K28 is serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), methionine (M), arginine (R), valine (V), tryptophan (W), or tyrosine (Y).

In some embodiments, the variant Sso7 polypeptide sequence is substantially (e.g., at least 60, 70, 80, 85, 90, or 95%) identical to any of, e.g., SEQ ID NOS: 27, 28, 29, 30, or 31, and comprises an amino acid other than R at the amino acid position corresponding to R43. In some embodiments, the amino acid position corresponding to R43 is alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

In some embodiments, the variant Sso7 polypeptide sequence is substantially (e.g., at least 60, 70, 80, 85, 90, or 95%) identical to any of, e.g., SEQ ID NOS: 27, 28, 29, 30, or 31, and comprises an amino acid other than K at the amino acid position corresponding to K28 and an amino acid other than R at the amino acid position corresponding to R43. For example, in some embodiments, the amino acid at position K28 is selected from: serine (S), threonine (T), cysteine (C), proline (P), aspartic acid (D), glutamic acid (E), asparagine (N), glutamine (Q), alanine (A), phenylalanine (F), glycine (G), histidine (H), isoleucine (I), leucine (L), valine (V), tryptophan (W), or tyrosine (Y) and the amino acid at position R43 is selected from: alanine (A), cytosine (C), aspartic acid (D), glutamic acid (E), phenylalanine (F), glycine (G), histidine (H), isoleucine (I), lysine (K), leucine (L), methionine (M), asparagine (N), glutamine (Q), serine (S), threonine (T), valine (V), tryptophan (W), tyrosine (Y), or proline (P).

V. Methods

In some embodiments, the fusion polypeptides described herein are used in nucleic acid amplification reactions. Such amplification reactions can include without limitation polymerase chain reaction (PCR), DNA ligase chain reaction (LCR), QBeta RNA replicase, and RNA transcription-based (such as TAS and 3SR) amplification reactions as well as others known to those of skill in the art. Polymerase chain reactions that can be conducted using the compositions described herein include without limitation reverse-transcription PCR (rt-PCR) and quantitative PCR (qPCR).

In some embodiments, the PCR is quantitative PCR in which the accumulation of amplicon is monitored in "real time" (i.e., continuously, e.g., once per cycle—rather than only following the completion of amplification). Quantitative amplification methods (e.g., quantitative PCR or quantitative linear amplification) can involve amplification of an nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002).

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also sometimes referred to as the TaqMan™ assay) (U.S. Pat. Nos. 5,210, 015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (e.g., the "TaqMan™ probe) during the amplification reaction. The fluorogenic probe consists of an oligonucleotide labeled with both a fluorescent reporter dye and a quencher dye. During PCR, this probe is cleaved by the 5'-3' exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., Light-Cycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In some embodiments, the PCR reaction mixture does not include a labeled probe oligonucleotide. For example, the reaction mixture lacks a Taqman or other labeled oligonucleotide probe for monitoring real-time or endpoint accumulation of the amplicon. In some of these embodiments, an intercalating fluorescent dye is included. In some embodiments, the intercalating dye changes signal (increases or decreases) when bound to double stranded nucleic acids compared to single stranded nucleic acids. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than or different from, for example, primer-dimers, non-specifically amplified sequences, etc.

A number of components of a PCR reaction are well known and can be determined readily by a skilled artisan. In certain aspects, it may be desirable to include an additional compound as an additive to improve efficiency in amplification reactions, such as qPCR. For example, there may be situations in which a polymerase of the invention that lacks exonuclease activity exhibits low efficiency for certain targets when used in a formulation that includes certain binding dyes (such as, in one non-limiting example, an EvaGreen DNA binding dye) or in the presence of certain amplification inhibitors. Such low efficiency may in some embodiments be a result of delay in Ct values associated with low input DNA concentrations. Methods for measuring efficiency of a particular reaction are known in the art.

In some embodiments, an osmolyte may be included in an amplification reaction of the invention to improve efficiency. See, e.g., WO2010/080910, incorporated by reference. Members of the osmolyte family have been shown to improve the thermal stability of proteins (Santoro, *Biochemistry*, 1992) as well as decrease DNA double helix stability (Chadalavada, FEBS Letters, 1997). Osmolytes of use in the present invention may include without limitation sarcosine, trimethylamine N-oxide (TMAO), dimethylsulfoniopropionate, and trimethylglycine. Sarcosine is chemically similar to betaine, a chemical which has been shown to improve conventional PCR (Henke, Nucleic Acids Research, 1997).

In conventional uses of osmolytes, the stabilizing effects of such compounds are generally observed at relatively high concentrations (>1M). However, in methods of the present invention, millimolar concentrations of osmolytes have been found to be effective for improving the reaction efficiency of amplification reactions such as qPCR. See, e.g., WO2010/080910, incorporated by reference. Without being bound by a mechanism of action, it is possible that the improvement in efficiency is the result of improvement of the Ct values for the reactions that contain low DNA template concentration. In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, or about 300 to about 350 mM osmolytes are used in methods and kits of the invention. In some embodiments, the osmolyte used in methods and kits of the invention is sarcosine. Indeed, it has been found that addition of sarcosine improved the efficiency of the amplification reaction as compared to control comprising water.

In some embodiments, particularly in the amplification of low-copy target nucleic acids or in the presence of amplification inhibitors, efficiency decreases due to the binding of polymerase to non-primed double-stranded nucleic acid targets. Binding of the polymerase to the double-stranded targets will prevent those targets from denaturation, hybridizing to primers, and undergoing an amplification reaction. To improve the specificity of the polymerase for primed templates, in some embodiments methods and kits of the invention utilize heparin. See, e.g., WO2010/080910, incorporated by reference. Heparin molecules, which are negatively charged, can be included in the reaction mixture to mimic the electrostatic property of double stranded nucleic acids. The addition of heparin can, without being limited to a mechanism of action, prevent excess polymerase from binding to the double-stranded template until a single-stranded primed-template becomes available. In some exemplary embodiments, heparin is used in methods and kits of the invention at concentrations of about 50 to about 750 pg/µl. In further exemplary embodiments, heparin is used in methods and kits of the invention at concentrations of about 75 to about 700, about 100 to about 600, about 125 to about 500, about 150 to about 400, about 175 to about 300, or about 200 to about 250 pg/µl.

Non-specific amplification can be reduced by reducing the formation of extension products from primers bound to non-target sequences prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization. In some embodiments, the polypeptides as described herein can be reversibly inactivated by a reagent bound to the polymerase. The inhibitory reagent can be removed by heat (e.g., above 50 or at 95° C.). Thus, in some embodiments, the amplification reaction comprises a hot start reagent.

In some embodiments, the reagent is a "hot start" antibody. Hot-start antibodies increase the specificity of amplification reactions, because they render the polymerase inactive at room temperature, thus avoiding extension of nonspecifically annealed primers or primer dimers. See, e.g., U.S. Pat. No. 5,338,671. The functional activity of the polymerase is restored by disassociating the antibody from the polymerase, generally through incubation at a higher temperature. In some embodiment, such a "higher temperature" is from about 90° to about 99° C. for about 2 to about 10 minutes. It will be appreciated that the temperature and length of time for incubation to disassociate the antibody and activate the polymerase can be varied according to known parameters to provide the most effective method of activating the polymerase in these hot-start methods. In other embodiments, the reagent is an aptamer that inhibits polymerase activity until the polymerase is heated to disassociate the aptamer. Exemplary aptamers include, but are not limited to, slow off-rate modified aptamers (e.g., SOMAmers™).

Alternatively, a polymerase can be substantially inactivated by covalently linking a chemical reagent to the polymerase. For example a dicarboxylic acid anhydride can be linked to one or more lysine residue of the polymerase, thereby substantially inactivating the polymerase activity. See, e.g., U.S. Pat. Nos. 5,773,258 and 5,677,152. The reagents are thermally labile and thus can be removed upon heating.

In some embodiments, the fusion polypeptide comprising a FEN1 protein or active fragment thereof can be used to generate a 5' cleaved primer flap that subsequently is used to prime a second amplification reaction to generate a detectable signal. An example of such a method includes the TOCE™ assay (Seegene, KR). Such assays detect a target nucleic acid sequence in which the PTO (Probing and Tagging Oligonucleotide) hybridized with the target nucleic acid sequence is cleaved to release a fragment and the fragment is hybridized with the CTO (Capturing and Templating Oligonucleotide) to form an extended duplex, followed by detecting the presence of the extended duplex. The extended duplex provides signals (generation, increase, extinguishment or decrease of signals) from labels indicating the presence of the extended duplex and has adjustable Tm value, which are well adoptable for detection of the presence of the target nucleic acid sequence. See, e.g., US Patent Publication No. 2013/0109588.

In other embodiments, the fusion polypeptide can be used to cause recombination between DNA strands, thereby replacing one strand of a DNA duplex with a homologous third strand. For example, the fusion polypeptide comprising 5'-3' exonuclease activity can be used to facilitate "somatic recombination" type of cross-linking

VI. Reaction Mixtures

The present invention also provides for reaction mixtures comprising one or more of the fusion polypeptides as described herein. Other reagents as described herein can also be included in the reaction mixture. For example, in some embodiments, the reaction mixtures comprise a fluorogenic probe comprises an oligonucleotide labeled with both a fluorescent reporter dye and a quencher dye that generates signal in a 5'-3' exonuclease "hydrolysis" PCR assay (also referred to as a TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)).

In some embodiments, the fusion polypeptides described herein have increased tolerance for common PCR inhibitors, e.g., inhibitors of Taq polymerase. Exemplary PCR inhibitors include, but are not limited to, heparin, bile salts, polysaccharides, collagen, heme, humic acid, melanin and eumelanin, urea, hemoglobin, lactoferrin, immunoglobulin G (IgG), and indigo dye. Thus in some embodiments the reaction mixture comprises a sample having inhibitors that would significantly inhibit activity of Taq polymerase (e.g., degrading Ct values by at least 1 compared to the Ct of a polymerase as described herein).

In some embodiments, the sample is a crude sample, i.e., a sample in which minimal or no purification of nucleic acids has occurred. For example, the crude sample can be a blood or serum sample, cell lysate, a plant or animal tissue sample, etc.

In some embodiments, the amplification reaction comprises dUTP and/or a nucleic acid template comprising incorporated uracil. In some embodiments, dUTP is included in an amplification reaction mixture so that amplification products can be prevented from contaminating future amplification reactions. This is achieved by an additional incubation step in the presence of the enzyme, UNG, followed by inactivation of UNG, prior to the amplification reactions. UNG renders uracil-containing templates unable to be amplified by polymerases.

In some embodiments, the target template to be amplified contains incorporated uracil. Polymerases having an active uracil-sensing domain (e.g., most or all native B family polymerases) typically stall at an incorporated uracil in the template. In contrast, polypeptides lacking an active USD as described herein will not stall at incorporated uracils.

In some embodiments, the reaction mixture is formulated as a ready-to-use formulation, meaning the mixture contains all components needed for a polymerase reaction except for a sample or except for a sample and oligonucleotide primers.

In some embodiments, the reaction mixture further comprises a reverse transcriptase and optionally reagents necessary for reverse transcription. Thus in some embodiments, the reaction mixture can be used to generate a cDNA from RNA in a sample and then the fusion polypeptide can subsequently amplify the cDNA in the same reaction mixture. Alternatively, the cDNA can be generated in a previous reverse transcription reaction and the resulting cDNA can be added to a reaction mixture in a two-step reaction (a first step for the RT reaction, and a second for the cDNA amplification).

VII. Polynucleotides

Also provided are polynucleotides encoding (1) a fusion polypeptide comprising a heterologous 5'-3' exonuclease domain and a polymerase (e.g., family B polymerase) as described herein or (2) a family B polymerase lacking the uracil sensing domain (USD). In some embodiments, the polynucleotides are isolated, i.e., are separated from the cell in which the polypeptide was translated and optionally purified. In some embodiments, expression cassettes (i.e., a heterologous promoter operably linked to the coding sequence) or vectors comprising the above-described polynucleotide are provided, as well as host cells (including but not limited to bacterial, fungal, yeast, insect, or mammalian cells) comprising such expression cassettes or vectors. Such host cells can be incubated under conditions to result in expression of the encoded polypeptide, which can subsequently be purified as desired.

VIII. Kits

In one aspect, kits comprising a fusion polypeptide as described herein is provided. Kits can be adapted, for example, for conducting nucleic acid amplification reactions. In some embodiments, such kits include dNTPs, and at least one buffer. Such kits may also include one or more primers as well as instructions for conducting nucleic acid amplification reactions using the components of the kits.

In still further embodiments, kits can include optimized buffer (e.g., Tris-HCl), KCl, $(NH_4)_2SO_4$, stabilizer, detergent, dNTPs, $MgCl_2$, and/or DMSO.

In still further embodiments, kits can include double stranded DNA binding dyes. Such double stranded DNA binding dyes can include without limitation: EvaGreen and SYBR Green, as well as any other double stranded DNA binding dyes known in the art.

Alternatively, or in addition, the kit can comprise one of more nucleic acid probe for use in a 5'-3' exonuclease "hydrolysis" PCR assay (also referred to as a TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™ probe") during the amplification reaction. The fluorogenic probe comprises an oligonucleotide labeled with both a fluorescent reporter dye and a quencher dye. During PCR, this probe is cleaved by the 5'-3' exonuclease activity of DNA polymerase if, and only if, it hybridizes to the segment being amplified. Cleavage of the probe generates an increase in the fluorescence intensity of the reporter dye.

It will be appreciated that kits can also encompass any combination of the above-described components.

The following examples are offered to illustrate, but not to limit the claimed invention.

EXAMPLES

Example 1

Proof-reading DNA polymerases, such as pfu DNA polymerase, oftentimes are hyper-thermalphilic (or highly thermal stable) and have ability to perform well in the presence of common DNA polymerase inhibitors, such as salt and solvent. These proof-reading DNA polymerases usually have a 3'-5' exonuclease activity that enhances fidelity; however they lack of 5'-3' exonuclease activity that is essential for signal generation in probe-based qPCR applications.

We constructed fusion DNA polymerases comprising a proof-reading DNA polymerase fused to two different flap endonucleases (Archaeon *Pyrococcus furiosus* flap endonuclease (pfu FEN1 SEQ ID NO:24)) and Archaeon *Desulfurococcus amylolyticus* flap endonuclease (Da FEN1 SEQ ID NO:10)). A flexible linker (SEQ ID NO:8) was used to link the carboxyl terminus of the flap endonuclease domain to the amino terminus of the polymerase. The polymerase used was a Pfu/Vent-hybrid DNA polymerase (SEQ ID NO: 20) and further included a carboxyl terminal Sso7d domain with a K28 mutation (SEQ ID NO: 22) and then a poly-His tag. The full length amino acid and coding sequence of the pfu FEN1-polymerase-Sso7d fusion (referred to as "fusion protein #1") as tested is SEQ ID NO:1 and 5, respectively. The full length amino acid and coding sequence of the Da FEN1-polymerase-Sso7d fusion (referred to as "fusion protein #2") as tested is SEQ ID NO:2 and 6, respectively.

We also constructed similar fusions, however without the uracil sensing domain (USD) of polymerase. In fact, in addition to the removal of the entire USD, a small number of additional amino acids were removed from the polymerase based on the predicted structure of the polymerase. The full length amino acid and coding sequence of the pfu FEN1-polymerase (USD minus)-Sso7d fusion (referred to as "fusion protein #3") as tested is SEQ ID NO:3 and 7, respectively. The full length amino acid and coding sequence of the Da FEN1-polymerase (USD minus)-Sso7d fusion (referred to as "fusion protein #4") as tested is SEQ ID NO:4 and 8, respectively.

The fusions were tested in a probe qPCR assay that required 5'-3' exonuclease activity to generate signal. As shown in the top part of FIG. 1, the positive control (Taq polymerase) generated signal in a concentration dependent manner. In contrast, the negative control (a pfu/DeepVent hybrid polymerase lacking 5'-3' exonuclease activity) did not generate significant signal. However, each of the above-described fusion proteins (fusions #1-4) had activity at least comparable to Taq.

Example 2

Taq polymerase has 5'-3' exonuclease activity but is generally considered to have a relatively low tolerance for the presence of inhibitors in the reaction mixture. In contrast, pfu and other family B polymerases lack 5'-3' exonuclease activity, but have a higher inhibitor tolerance. We tested one of the fusions described herein (Pfu FEN1 fused to a Pfu/DeepVent hybrid DNA polymerase (SEQ ID NO:20) and an Sso7d domain) to determine whether the protein fusions retain the higher inhibitor tolerance of the B family polymerases with the fusion of the 5'-3' exonuclease domain. iSTaq DNA polymerase (a fusion Sso7d DNA-binding protein and Taq DNA polymerase) was used as a control polymerase in these experiments. The effect of the following inhibitors was tested: heparin with ammonium and sodium salt, hematin, and humic acid. Inhibitor tolerance is reported in term of Cq value.

| | Heparin Ammonium Salt | |
| --- | --- | --- |
| ng per 20 ul reaction | iSTaq Pol (Control) Cq value | fusion protein #1 (Test) Cq value |
| 0 | 16.3 | 16.0 |
| 0.4 | 16.3 | 16.1 |
| 1.6 | 17.1 | 16.1 |
| 6.3 | n.d. | 16.0 |
| 25 | n.d. | 18.5 |

| | Heparin Sodium Salt | |
| --- | --- | --- |
| ng per 20 ul reaction | iSTaq Pol (Control) Cq value | fusion protein #1 (Test) Cq value |
| 0 | 16.2 | 16.3 |
| 0.4 | 16.0 | 16.2 |
| 1.6 | 17.3 | 15.9 |
| 6.3 | n.d. | 15.8 |
| 25 | n.d. | 21.7 |

| | Hematin | |
| --- | --- | --- |
| nM | iSTaq Pol (Control) Cq value | fusion protein #1 (Test) Cq value |
| 0 | 16.2 | 16.1 |
| 150 | 15.8 | 15.8 |
| 187.5 | 16.8 | 15.7 |
| 225 | 29.6 | 16.0 |
| 262.5 | 38.2 | 16.1 |
| 300 | n.d. | 29.4 |

| Humic Acid | | |
|---|---|---|
| ng per 20 ul reaction | iSTaq Pol (Control) Cq value | fusion protein #1 (Test) Cq value |
| 0 | 16.0 | 16.2 |
| 0.8 | 16.0 | 16.1 |
| 3.1 | 18.7 | 16.0 |
| 12.5 | n.d. | 27.2 |
| 50 | n.d. | n.d. |

As shown in the data above, the 5'-3' exonuclease-Pfu/DeepVent hybrid DNA polymerase-Sso7d fusion had a higher tolerance for a variety of inhibitors compared to the Taq polymerase-based Sso7d fusion, demonstrating that the fusions described herein retain the higher inhibitor tolerance of the family B polymerases even when fused to the 5'-3' exonuclease domain.

Example 3

A fusion DNA polymerases comprising a proof-reading DNA polymerase (SEQ ID NO: 20) was fused to 5'-3' exonuclease domain of Taq polymerase 5'-3' exonuclease domain (SEQ ID NO:35). The resulting DNA and amino acid sequence of the fusion was SEQ ID NO: 32 and 33, respectively. A flexible linker (SEQ ID NO:37) was used to link the carboxyl terminus of the 5'-3' exonuclease domain to the amino terminus of the polymerase. The fusion was further fused with a carboxyl terminal Sso7d domain with a K28 mutation (SEQ ID NO: 22) and then a poly-His tag.

Figure 4:
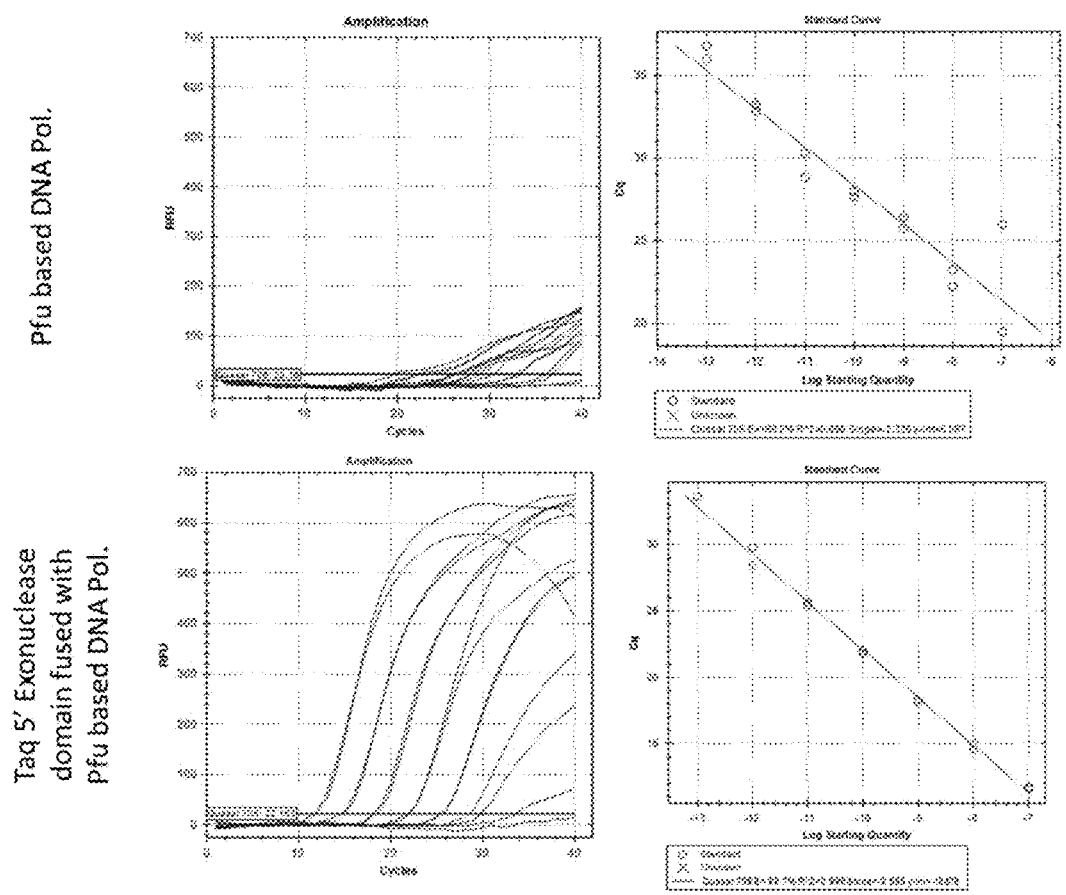
FIG. 4 illustrates results of quantitative detection of probe-based qPCR reactions using a PFU/DEEPVENT polymerase alone (upper) or a Taq 5'-3' exonuclease domain fused to the PFU/DEEPVENT polymerase (lower) as explained in Example 3.

FIG. 4 (lower portion) demonstrates that, in a probe-based qPCR assay, a fusion polymerase with the Taq polymerase 5'-3' exonuclease domain can amplify DNA targets and generate detection signal through probe hydrolysis. In contrast, a polymerase lack of Taq polymerase 5'-3' exonuclease domain cannot generate detectable signal (FIG. 4).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polypeptide having polymerase activity and 5'-3' exonuclease activity, the polypeptide comprising a 5'-3' exonuclease domain linked to a heterologous polymerase that does not naturally have 5'-3' exonuclease activity, wherein the heterologous polymerase comprises a family B polymerase catalytic domain having polymerase activity and the 5'-3' exonuclease domain is a flap endonuclease, wherein the polypeptide substantially lacks 3'-5' exonuclease activity.

2. The polypeptide of claim 1, wherein the polymerase activity and 5'-3' exonuclease activity are thermostable.

3. The polypeptide of claim 1, further comprising a heterologous sequence non-specific double-stranded DNA binding domain or sequence non-specific single-stranded DNA binding domain.

4. The polypeptide of claim 3, wherein the heterologous sequence non-specific double stranded DNA binding domain comprises a Sso7 DNA binding domain or a Sso7-like DNA binding domain.

5. The polypeptide of claim 4, wherein the heterologous sequence non-specific double stranded DNA binding domain is at least 60% identical to any of SEQ ID NOs: 27, 28, 29, 30, or 31.

6. The polypeptide of claim 1, wherein the 5'-3' exonuclease domain and the family B polymerase catalytic domain are linked by a linker.

7. The polypeptide of claim 6, wherein the linker is an amino acid linker.

8. The polypeptide of claim 1, wherein the carboxyl terminus of the 5'-3' exonuclease domain is linked via a linker to the amino terminus of the family B polymerase catalytic domain.

9. The polypeptide of claim 1, wherein the polymerase comprises a deletion that substantially eliminates 3'-5' exonuclease activity.

10. A reaction mixture comprising the polypeptide of claim 1.

11. The reaction mixture of claim 10, further comprising a polynucleotide primer.

12. The reaction mixture of claim 10, wherein the reaction mixture comprises a sample nucleic acid.

13. A method of performing polymerase chain reaction (PCR), the method comprising:
   contacting in an amplification reaction mixture the polypeptide of claim 1 to a sample comprising nucleic acids under conditions to allow for amplification of a target sequence in the nucleic acids, if present; and
   detecting the presence or absence of amplified target sequence.

14. The polypeptide of claim 5, wherein the heterologous sequence non-specific double stranded DNA binding domain is at least 95% identical to any of SEQ ID NOs: 27, 28, 29, 30, or 31.

15. The polypeptide of claim 7, wherein the amino acid linker is between 1-50 amino acids in length.

* * * * *

SEQUENCE LISTING

```
<160> NUMBER OF SEQ ID NOS: 41

<210> SEQ ID NO 1
<211> LENGTH: 1195
<212> TYPE: PRT
<213> ORGANISM: Artificial Sequence
<220> FEATURE:
<223> OTHER INFORMATION: synthetic full length Pfu FEN1-polymerase-Sso7d
      fusion DNA polymerase, fusion protein #1, Archaeon Pyrococcus
      furiosus flap endonuclease (Pfu FEN1) fused to Sulfolobus
      solfataricus Sso7d

<400> SEQUENCE: 1

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
                20                  25                  30

Tyr Gln Phe Leu Ser Thr Ile Arg Gln Lys Asp Gly Thr Pro Leu Met
            35                  40                  45

Asp Ser Lys Gly Arg Ile Thr Ser His Leu Ser Gly Leu Phe Tyr Arg
        50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Lys Glu Leu Glu Lys Arg Arg Glu
                85                  90                  95

Ala Arg Glu Glu Ala Glu Glu Lys Trp Arg Glu Ala Leu Glu Lys Gly
                100                 105                 110

Glu Ile Glu Glu Ala Arg Lys Tyr Ala Gln Arg Ala Thr Arg Val Asn
            115                 120                 125

Glu Met Leu Ile Glu Asp Ala Lys Lys Leu Leu Glu Leu Met Gly Ile
        130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175

Leu Leu Phe Gly Ala Pro Arg Leu Val Arg Asn Leu Thr Ile Thr Gly
                180                 185                 190
```

```
Lys Arg Lys Leu Pro Gly Lys Asn Val Tyr Val Glu Ile Lys Pro Glu
        195                 200                 205

Leu Ile Ile Leu Glu Glu Val Leu Lys Glu Leu Lys Leu Thr Arg Glu
        210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                245                 250                 255

Ser Lys Asp Pro Leu Ala Lys Phe Gln Lys Gln Ser Asp Val Asp Leu
            260                 265                 270

Tyr Ala Ile Lys Glu Phe Phe Leu Asn Pro Val Thr Asp Asn Tyr
            275                 280                 285

Asn Leu Val Trp Arg Asp Pro Asp Glu Glu Gly Ile Leu Lys Phe Leu
        290                 295                 300

Cys Asp Glu His Asp Phe Ser Glu Glu Arg Val Lys Asn Gly Leu Glu
305                 310                 315                 320

Arg Leu Lys Lys Ala Ile Lys Ser Gly Gly Ser Gly Gly Gly
                325                 330                 335

Ser Gly Gly Gly Ser Ile Leu Asp Ala Asp Tyr Ile Thr Glu Glu
                340                 345                 350

Gly Lys Pro Val Ile Arg Leu Phe Lys Lys Glu Asn Gly Glu Phe Lys
        355                 360                 365

Ile Glu His Asp Arg Thr Phe Arg Pro Tyr Ile Tyr Ala Leu Leu Lys
        370                 375                 380

Asp Asp Ser Lys Ile Glu Val Lys Lys Ile Thr Ala Glu Arg His
385                 390                 395                 400

Gly Lys Ile Val Arg Ile Val Asp Ala Glu Lys Val Glu Lys Lys Phe
                405                 410                 415

Leu Gly Arg Pro Ile Thr Val Trp Arg Leu Tyr Phe Glu His Pro Gln
            420                 425                 430

Asp Val Pro Thr Ile Arg Glu Lys Ile Arg Glu His Ser Ala Val Val
            435                 440                 445

Asp Ile Phe Glu Tyr Asp Ile Pro Phe Ala Lys Arg Tyr Leu Ile Asp
        450                 455                 460

Lys Gly Leu Ile Pro Met Glu Gly Asp Glu Glu Leu Lys Leu Leu Ala
465                 470                 475                 480

Phe Ala Ile Ala Thr Leu Tyr His Glu Gly Glu Glu Phe Gly Lys Gly
                485                 490                 495

Pro Ile Ile Met Ile Ser Tyr Ala Asp Glu Glu Ala Lys Val Ile
            500                 505                 510

Thr Trp Lys Lys Ile Asp Leu Pro Tyr Val Glu Val Val Ser Ser Glu
            515                 520                 525

Arg Glu Met Ile Lys Arg Phe Leu Lys Ile Ile Arg Glu Lys Asp Pro
        530                 535                 540

Asp Ile Ile Ile Thr Tyr Asn Gly Asp Ser Phe Asp Leu Pro Tyr Leu
545                 550                 555                 560

Ala Lys Arg Ala Glu Lys Leu Gly Ile Lys Leu Thr Ile Gly Arg Asp
                565                 570                 575

Gly Ser Glu Pro Lys Met Gln Arg Ile Gly Asp Met Thr Ala Val Glu
            580                 585                 590

Val Lys Gly Arg Ile His Phe Asp Leu Tyr His Val Ile Arg Arg Thr
            595                 600                 605
```

```
Ile Asn Leu Pro Thr Tyr Thr Leu Glu Ala Val Tyr Glu Ala Ile Phe
610                 615                 620
Gly Lys Pro Lys Glu Lys Val Tyr Ala Asp Glu Ile Ala Lys Ala Trp
625                 630                 635                 640
Glu Thr Gly Glu Gly Leu Glu Arg Val Ala Lys Tyr Ser Met Glu Asp
                645                 650                 655
Ala Lys Ala Thr Tyr Glu Leu Gly Lys Glu Phe Phe Pro Met Glu Ala
                660                 665                 670
Gln Leu Ser Arg Leu Val Gly Gln Pro Leu Trp Asp Val Ser Arg Ser
            675                 680                 685
Ser Thr Gly Asn Leu Val Glu Trp Phe Leu Leu Arg Lys Ala Tyr Glu
690                 695                 700
Arg Asn Glu Leu Ala Pro Asn Lys Pro Asp Glu Arg Glu Tyr Glu Arg
705                 710                 715                 720
Arg Leu Arg Glu Ser Tyr Ala Gly Gly Phe Val Lys Glu Pro Glu Lys
                725                 730                 735
Gly Leu Trp Glu Asn Ile Val Ser Leu Asp Phe Arg Ala Leu Tyr Pro
                740                 745                 750
Ser Ile Ile Ile Thr His Asn Val Ser Pro Asp Thr Leu Asn Arg Glu
            755                 760                 765
Gly Cys Arg Asn Tyr Asp Val Ala Pro Glu Val Gly His Lys Phe Cys
770                 775                 780
Lys Asp Phe Pro Gly Phe Ile Pro Ser Leu Leu Lys Arg Leu Leu Asp
785                 790                 795                 800
Glu Arg Gln Lys Ile Lys Thr Lys Met Lys Ala Ser Gln Asp Pro Ile
                805                 810                 815
Glu Lys Ile Met Leu Asp Tyr Arg Gln Arg Ala Ile Lys Ile Leu Ala
                820                 825                 830
Asn Ser Tyr Tyr Gly Tyr Tyr Gly Tyr Ala Lys Ala Arg Trp Tyr Cys
            835                 840                 845
Lys Glu Cys Ala Glu Ser Val Thr Ala Trp Gly Arg Glu Tyr Ile Glu
850                 855                 860
Phe Val Trp Lys Glu Leu Glu Glu Lys Phe Gly Phe Lys Val Leu Tyr
865                 870                 875                 880
Ile Asp Thr Asp Gly Leu Tyr Ala Thr Ile Pro Gly Gly Lys Ser Glu
                885                 890                 895
Glu Ile Lys Lys Lys Ala Leu Glu Phe Val Asp Tyr Ile Asn Ala Lys
                900                 905                 910
Leu Pro Gly Leu Leu Glu Leu Glu Tyr Glu Gly Phe Tyr Lys Arg Gly
            915                 920                 925
Phe Phe Val Thr Lys Lys Lys Tyr Ala Leu Ile Asp Glu Glu Gly Lys
930                 935                 940
Ile Ile Thr Arg Gly Leu Glu Ile Val Arg Arg Asp Trp Ser Glu Ile
945                 950                 955                 960
Ala Lys Glu Thr Gln Ala Arg Val Leu Glu Ala Ile Leu Lys His Gly
                965                 970                 975
Asn Val Glu Glu Ala Val Arg Ile Val Lys Glu Val Thr Gln Lys Leu
                980                 985                 990
Ser Lys Tyr Glu Ile Pro Pro Glu Lys Leu Ala Ile Tyr Glu Gln Ile
            995                 1000                1005
Thr Arg Pro Leu His Glu Tyr Lys Ala Ile Gly Pro His Val Ala Val
            1010                1015                1020
Ala Lys Arg Leu Ala Ala Lys Gly Val Lys Ile Lys Pro Gly Met Val
```

-continued

```
1025                1030                1035                1040
Ile Gly Tyr Ile Val Leu Arg Gly Asp Gly Pro Ile Ser Asn Arg Ala
                1045                1050                1055
Ile Leu Ala Glu Glu Tyr Asp Pro Arg Lys His Lys Tyr Asp Ala Glu
                1060                1065                1070
Tyr Tyr Ile Glu Asn Gln Val Leu Pro Ala Val Leu Arg Ile Leu Glu
                1075                1080                1085
Gly Phe Gly Tyr Arg Lys Glu Asp Leu Arg Trp Gln Lys Thr Lys Gln
                1090                1095                1100
Thr Gly Leu Thr Ser Trp Leu Asn Ile Lys Lys Ser Gly Thr Gly Gly
1105                1110                1115                1120
Gly Gly Ala Thr Val Lys Phe Lys Tyr Lys Gly Glu Lys Glu Val
                1125                1130                1135
Asp Ile Ser Lys Ile Lys Lys Val Trp Arg Val Gly Pro Met Ile Ser
                1140                1145                1150
Phe Thr Tyr Asp Glu Gly Gly Gly Lys Thr Gly Arg Gly Ala Val Ser
                1155                1160                1165
Glu Lys Asp Ala Pro Lys Glu Leu Leu Gln Met Leu Glu Lys Gln Lys
                1170                1175                1180
Ala Ala Ala Leu Glu His His His His His His
1185                1190                1195

<210> SEQ ID NO 2
<211> LENGTH: 1070
<212> TYPE: PRT
<213> ORGANISM: Artificial Sequence
<220> FEATURE:
<223> OTHER INFORMATION: synthetic full length Da FEN1-polymerase-Sso7d
      fusion DNA polymerase, fusion protein #2, Archaeon
      Desulfurococcus amylolyticus flap endonuclease (Da
      FEN1) fused to Sulfolobus solfataricus Sso7d

<400> SEQUENCE: 2

Met Gly Val Pro Ile Gly Glu Ile Ile Pro Arg Lys Glu Ile Glu Leu
 1               5                   10                  15
Glu Asn Leu Tyr Gly Lys Lys Ile Ala Ile Asp Ala Leu Asn Ala Ile
                20                  25                  30
Tyr Gln Phe Leu Ser Thr Ile Arg Gln Lys Asp Gly Thr Pro Leu Met
            35                  40                  45
Asp Ser Lys Gly Arg Ile Thr Ser His Leu Ser Gly Leu Phe Tyr Arg
        50                  55                  60
Thr Ile Asn Leu Met Glu Ala Gly Ile Lys Pro Val Tyr Val Phe Asp
65                  70                  75                  80
Gly Glu Pro Pro Glu Phe Lys Lys Lys Glu Leu Glu Lys Arg Arg Glu
                85                  90                  95
Ala Arg Glu Glu Ala Glu Lys Trp Arg Glu Ala Leu Glu Lys Gly
                100                 105                 110
Glu Ile Glu Glu Ala Arg Lys Tyr Ala Gln Arg Ala Thr Arg Val Asn
            115                 120                 125
Glu Met Leu Ile Glu Asp Ala Lys Lys Leu Leu Glu Leu Met Gly Ile
        130                 135                 140
Pro Ile Val Gln Ala Pro Ser Glu Gly Glu Ala Gln Ala Ala Tyr Met
145                 150                 155                 160
Ala Ala Lys Gly Ser Val Tyr Ala Ser Ala Ser Gln Asp Tyr Asp Ser
                165                 170                 175
Leu Leu Phe Gly Ala Pro Arg Leu Val Arg Asn Leu Thr Ile Thr Gly
```

-continued

```
            180                 185                 190
Lys Arg Lys Leu Pro Gly Lys Asn Val Tyr Val Glu Ile Lys Pro Glu
            195                 200                 205
Leu Ile Ile Leu Glu Glu Val Leu Lys Glu Leu Lys Leu Thr Arg Glu
210                 215                 220
Lys Leu Ile Glu Leu Ala Ile Leu Val Gly Thr Asp Tyr Asn Pro Gly
225                 230                 235                 240
Gly Ile Lys Gly Ile Gly Leu Lys Lys Ala Leu Glu Ile Val Arg His
                    245                 250                 255
Ser Lys Asp Pro Leu Ala Lys Phe Gln Lys Gln Ser Asp Val Asp Leu
            260                 265                 270
Tyr Ala Ile Lys Glu Phe Phe Leu Asn Pro Val Thr Asp Asn Tyr
            275                 280                 285
Asn Leu Val Trp Arg Asp Pro Asp Glu Glu Gly Ile Leu Lys Phe Leu
            290                 295                 300
Cys Asp Glu His Asp Phe Ser Glu Glu Arg Val Lys Asn Gly Leu Glu
305                 310                 315                 320
Arg Leu Lys Lys Ala Ile Lys Ser Gly Gly Ser Gly Gly Gly Gly
                    325                 330                 335
Ser Gly Gly Gly Gly Ser Ile Pro Met Glu Gly Asp Glu Glu Leu Lys
            340                 345                 350
Leu Leu Ala Phe Ala Ile Ala Thr Leu Tyr His Glu Gly Glu Glu Phe
            355                 360                 365
Gly Lys Gly Pro Ile Ile Met Ile Ser Tyr Ala Asp Glu Glu Glu Ala
370                 375                 380
Lys Val Ile Thr Trp Lys Lys Ile Asp Leu Pro Tyr Val Glu Val Val
385                 390                 395                 400
Ser Ser Glu Arg Glu Met Ile Lys Arg Phe Leu Lys Ile Ile Arg Glu
                    405                 410                 415
Lys Asp Pro Asp Ile Ile Ile Thr Tyr Asn Gly Asp Ser Phe Asp Leu
            420                 425                 430
Pro Tyr Leu Ala Lys Arg Ala Glu Lys Leu Gly Ile Lys Leu Thr Ile
            435                 440                 445
Gly Arg Asp Gly Ser Glu Pro Lys Met Gln Arg Ile Gly Asp Met Thr
            450                 455                 460
Ala Val Glu Val Lys Gly Arg Ile His Phe Asp Leu Tyr His Val Ile
465                 470                 475                 480
Arg Arg Thr Ile Asn Leu Pro Thr Tyr Thr Leu Glu Ala Val Tyr Glu
                    485                 490                 495
Ala Ile Phe Gly Lys Pro Lys Glu Lys Val Tyr Ala Asp Glu Ile Ala
            500                 505                 510
Lys Ala Trp Glu Thr Gly Glu Gly Leu Glu Arg Val Ala Lys Tyr Ser
            515                 520                 525
Met Glu Asp Ala Lys Ala Thr Tyr Glu Leu Gly Lys Glu Phe Phe Pro
            530                 535                 540
Met Glu Ala Gln Leu Ser Arg Leu Val Gly Gln Pro Leu Trp Asp Val
545                 550                 555                 560
Ser Arg Ser Ser Thr Gly Asn Leu Val Glu Trp Phe Leu Leu Arg Lys
                    565                 570                 575
Ala Tyr Glu Arg Asn Glu Leu Ala Pro Asn Lys Pro Asp Glu Arg Glu
            580                 585                 590
Tyr Glu Arg Arg Leu Arg Glu Ser Tyr Ala Gly Gly Phe Val Lys Glu
            595                 600                 605
```

-continued

```
Pro Glu Lys Gly Leu Trp Glu Asn Ile Val Ser Leu Asp Phe Arg Ala
610                 615                 620
Leu Tyr Pro Ser Ile Ile Ile Thr His Asn Val Ser Pro Asp Thr Leu
625                 630                 635                 640
Asn Arg Glu Gly Cys Arg Asn Tyr Asp Val Ala Pro Glu Val Gly His
            645                 650                 655
Lys Phe Cys Lys Asp Phe Pro Gly Phe Ile Pro Ser Leu Leu Lys Arg
            660                 665                 670
Leu Leu Asp Glu Arg Gln Lys Ile Lys Thr Lys Met Lys Ala Ser Gln
        675                 680                 685
Asp Pro Ile Glu Lys Ile Met Leu Asp Tyr Arg Gln Arg Ala Ile Lys
    690                 695                 700
Ile Leu Ala Asn Ser Tyr Tyr Gly Tyr Tyr Gly Tyr Ala Lys Ala Arg
705                 710                 715                 720
Trp Tyr Cys Lys Glu Cys Ala Glu Ser Val Thr Ala Trp Gly Arg Glu
            725                 730                 735
Tyr Ile Glu Phe Val Trp Lys Glu Leu Glu Glu Lys Phe Gly Phe Lys
            740                 745                 750
Val Leu Tyr Ile Asp Thr Asp Gly Leu Tyr Ala Thr Ile Pro Gly Gly
        755                 760                 765
Lys Ser Glu Glu Ile Lys Lys Lys Ala Leu Glu Phe Val Asp Tyr Ile
770                 775                 780
Asn Ala Lys Leu Pro Gly Leu Leu Glu Leu Glu Tyr Glu Gly Phe Tyr
785                 790                 795                 800
Lys Arg Gly Phe Phe Val Thr Lys Lys Lys Tyr Ala Leu Ile Asp Glu
            805                 810                 815
Glu Gly Lys Ile Ile Thr Arg Gly Leu Glu Ile Val Arg Arg Asp Trp
            820                 825                 830
Ser Glu Ile Ala Lys Glu Thr Gln Ala Arg Val Leu Glu Ala Ile Leu
        835                 840                 845
Lys His Gly Asn Val Glu Glu Ala Val Arg Ile Val Lys Glu Val Thr
    850                 855                 860
Gln Lys Leu Ser Lys Tyr Glu Ile Pro Pro Glu Lys Leu Ala Ile Tyr
865                 870                 875                 880
Glu Gln Ile Thr Arg Pro Leu His Glu Tyr Lys Ala Ile Gly Pro His
            885                 890                 895
Val Ala Val Ala Lys Arg Leu Ala Ala Lys Gly Val Lys Ile Lys Pro
            900                 905                 910
Gly Met Val Ile Gly Tyr Ile Val Leu Arg Gly Asp Gly Pro Ile Ser
        915                 920                 925
Asn Arg Ala Ile Leu Ala Glu Glu Tyr Asp Pro Arg Lys His Lys Tyr
    930                 935                 940
Asp Ala Glu Tyr Tyr Ile Glu Asn Gln Val Leu Pro Ala Val Leu Arg
945                 950                 955                 960
Ile Leu Glu Gly Phe Gly Tyr Arg Lys Glu Asp Leu Arg Trp Gln Lys
            965                 970                 975
Thr Lys Gln Thr Gly Leu Thr Ser Trp Leu Asn Ile Lys Lys Ser Gly
            980                 985                 990
Thr Gly Gly Gly Gly Ala Thr Val Lys Phe Lys Tyr Lys Gly Glu Glu
        995                 1000                1005
Lys Glu Val Asp Ile Ser Lys Ile Lys Lys Val Trp Arg Val Gly Pro
    1010                1015                1020
```

```
Met Ile Ser Phe Thr Tyr Asp Glu Gly Gly Lys Thr Gly Arg Gly
1025                1030                1035                1040

Ala Val Ser Glu Lys Asp Ala Pro Lys Glu Leu Leu Gln Met Leu Glu
            1045                1050                1055

Lys Gln Lys Ala Ala Ala Leu Glu His His His His His His
            1060                1065                1070
```

<210> SEQ ID NO 3
<211> LENGTH: 1221
<212> TYPE: PRT
<213> ORGANISM: Artificial Sequence
<220> FEATURE:
<223> OTHER INFORMATION: synthetic full length Pfu FEN1-polymerase (USD minus)-Sso7d fusion DNA polymerase, fusion protein #3, Archaeon Pyrococcus furiosus flap endonuclease (Pfu FEN1) without uracil sensing domain (USD) fused to Sulfolobus solfataricus Sso7d

<400> SEQUENCE: 3

```
Met Gly Val Asp Leu Lys Asp Ile Ile Pro Gly Glu Ala Lys Thr Val
1               5                   10                  15

Ile Glu Asp Leu Arg Ile Leu His Gly Lys Ile Val Ile Asp Gly
            20                  25                  30

Tyr Asn Ala Leu Tyr Gln Phe Leu Ala Ala Ile Arg Gln Pro Asp Gly
            35                  40                  45

Thr Pro Leu Met Asp Asn Asn Gly Arg Ile Thr Ser His Leu Ser Gly
50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
            100                 105                 110

Val Gln Ser Gly Asp Leu Glu Leu Ala Arg Arg Tyr Ala Met Met Ser
            115                 120                 125

Ala Lys Leu Thr Glu Glu Met Val Arg Asp Ala Lys Ser Leu Leu Asp
130                 135                 140

Ala Met Gly Ile Pro Trp Val Gln Ala Pro Ala Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
            195                 200                 205

Val Lys Pro Glu Leu Ile Glu Leu Asp Lys Leu Leu Val Gln Leu Gly
            210                 215                 220

Ile Thr Leu Glu Asn Leu Ile Asp Ile Gly Ile Leu Leu Gly Thr Asp
225                 230                 235                 240

Tyr Asn Pro Asp Gly Phe Glu Gly Ile Gly Pro Lys Lys Ala Leu Gln
                245                 250                 255

Leu Val Lys Ala Tyr Gly Gly Ile Glu Lys Ile Pro Lys Pro Ile Leu
            260                 265                 270

Lys Ser Pro Ile Glu Val Asp Val Ile Ala Ile Lys Lys Tyr Phe Leu
            275                 280                 285

Gln Pro Gln Val Thr Asp Asn Tyr Arg Ile Glu Trp His Thr Pro Asp
290                 295                 300
```

-continued

```
Pro Asp Ala Val Lys Arg Ile Leu Val Asp Glu His Asp Phe Ser Ile
305                 310                 315                 320

Asp Arg Val Ser Thr Ala Leu Glu Arg Tyr Val Lys Ala Phe Lys Glu
            325                 330                 335

Asn Ile Arg Gly Glu Gln Lys Gly Leu Ser Lys Trp Phe Ser Lys Pro
        340                 345                 350

Lys Ser Gly Gly Ser Gly Gly Gly Gly Ser Gly Gly Gly Gly Ser
    355                 360                 365

Ile Leu Asp Ala Asp Tyr Ile Thr Glu Glu Gly Lys Pro Val Ile Arg
    370                 375                 380

Leu Phe Lys Lys Glu Asn Gly Glu Phe Lys Ile Glu His Asp Arg Thr
385                 390                 395                 400

Phe Arg Pro Tyr Ile Tyr Ala Leu Leu Lys Asp Asp Ser Lys Ile Glu
            405                 410                 415

Glu Val Lys Lys Ile Thr Ala Glu Arg His Gly Lys Ile Val Arg Ile
        420                 425                 430

Val Asp Ala Glu Lys Val Glu Lys Lys Phe Leu Gly Arg Pro Ile Thr
    435                 440                 445

Val Trp Arg Leu Tyr Phe Glu His Pro Gln Asp Val Pro Thr Ile Arg
450                 455                 460

Glu Lys Ile Arg Glu His Ser Ala Val Val Asp Ile Phe Glu Tyr Asp
465                 470                 475                 480

Ile Pro Phe Ala Lys Arg Tyr Leu Ile Asp Lys Gly Leu Ile Pro Met
            485                 490                 495

Glu Gly Asp Glu Glu Leu Lys Leu Leu Ala Phe Ala Ile Ala Thr Leu
        500                 505                 510

Tyr His Glu Gly Glu Glu Phe Gly Lys Gly Pro Ile Ile Met Ile Ser
    515                 520                 525

Tyr Ala Asp Glu Glu Ala Lys Val Ile Thr Trp Lys Lys Ile Asp
    530                 535                 540

Leu Pro Tyr Val Glu Val Val Ser Ser Glu Arg Glu Met Ile Lys Arg
545                 550                 555                 560

Phe Leu Lys Ile Ile Arg Glu Lys Asp Pro Asp Ile Ile Ile Thr Tyr
            565                 570                 575

Asn Gly Asp Ser Phe Asp Leu Pro Tyr Leu Ala Lys Arg Ala Glu Lys
        580                 585                 590

Leu Gly Ile Lys Leu Thr Ile Gly Arg Asp Gly Ser Glu Pro Lys Met
    595                 600                 605

Gln Arg Ile Gly Asp Met Thr Ala Val Glu Val Lys Gly Arg Ile His
    610                 615                 620

Phe Asp Leu Tyr His Val Ile Arg Arg Thr Ile Asn Leu Pro Thr Tyr
625                 630                 635                 640

Thr Leu Glu Ala Val Tyr Glu Ala Ile Phe Gly Lys Pro Lys Glu Lys
            645                 650                 655

Val Tyr Ala Asp Glu Ile Ala Lys Ala Trp Glu Thr Gly Glu Gly Leu
        660                 665                 670

Glu Arg Val Ala Lys Tyr Ser Met Glu Asp Ala Lys Ala Thr Tyr Glu
    675                 680                 685

Leu Gly Lys Glu Phe Phe Pro Met Glu Ala Gln Leu Ser Arg Leu Val
    690                 695                 700

Gly Gln Pro Leu Trp Asp Val Ser Arg Ser Ser Thr Gly Asn Leu Val
705                 710                 715                 720

Glu Trp Phe Leu Leu Arg Lys Ala Tyr Glu Arg Asn Glu Leu Ala Pro
```

```
                    725                 730                 735
Asn Lys Pro Asp Glu Arg Glu Tyr Glu Arg Arg Leu Arg Glu Ser Tyr
                740                 745                 750
Ala Gly Gly Phe Val Lys Glu Pro Glu Lys Gly Leu Trp Glu Asn Ile
                755                 760                 765
Val Ser Leu Asp Phe Arg Ala Leu Tyr Pro Ser Ile Ile Ile Thr His
            770                 775                 780
Asn Val Ser Pro Asp Thr Leu Asn Arg Glu Gly Cys Arg Asn Tyr Asp
785                 790                 795                 800
Val Ala Pro Glu Val Gly His Lys Phe Cys Lys Asp Phe Pro Gly Phe
                805                 810                 815
Ile Pro Ser Leu Leu Lys Arg Leu Leu Asp Glu Arg Gln Lys Ile Lys
                820                 825                 830
Thr Lys Met Lys Ala Ser Gln Asp Pro Ile Glu Lys Ile Met Leu Asp
                835                 840                 845
Tyr Arg Gln Arg Ala Ile Lys Ile Leu Ala Asn Ser Tyr Tyr Gly Tyr
            850                 855                 860
Tyr Gly Tyr Ala Lys Ala Arg Trp Tyr Cys Lys Glu Cys Ala Glu Ser
865                 870                 875                 880
Val Thr Ala Trp Gly Arg Glu Tyr Ile Glu Phe Val Trp Lys Glu Leu
                885                 890                 895
Glu Glu Lys Phe Gly Phe Lys Val Leu Tyr Ile Asp Thr Asp Gly Leu
                900                 905                 910
Tyr Ala Thr Ile Pro Gly Gly Lys Ser Glu Glu Ile Lys Lys Lys Ala
                915                 920                 925
Leu Glu Phe Val Asp Tyr Ile Asn Ala Lys Leu Pro Gly Leu Leu Glu
            930                 935                 940
Leu Glu Tyr Glu Gly Phe Tyr Lys Arg Gly Phe Phe Val Thr Lys Lys
945                 950                 955                 960
Lys Tyr Ala Leu Ile Asp Glu Glu Gly Lys Ile Ile Thr Arg Gly Leu
                965                 970                 975
Glu Ile Val Arg Arg Asp Trp Ser Glu Ile Ala Lys Glu Thr Gln Ala
                980                 985                 990
Arg Val Leu Glu Ala Ile Leu Lys His Gly Asn Val Glu Glu Ala Val
            995                 1000                1005
Arg Ile Val Lys Glu Val Thr Gln Lys Leu Ser Lys Tyr Glu Ile Pro
            1010                1015                1020
Pro Glu Lys Leu Ala Ile Tyr Glu Gln Ile Thr Arg Pro Leu His Glu
1025                1030                1035                1040
Tyr Lys Ala Ile Gly Pro His Val Ala Val Ala Lys Arg Leu Ala Ala
                1045                1050                1055
Lys Gly Val Lys Ile Lys Pro Gly Met Val Ile Gly Tyr Ile Val Leu
                1060                1065                1070
Arg Gly Asp Gly Pro Ile Ser Asn Arg Ala Ile Leu Ala Glu Glu Tyr
            1075                1080                1085
Asp Pro Arg Lys His Lys Tyr Asp Ala Glu Tyr Tyr Ile Glu Asn Gln
            1090                1095                1100
Val Leu Pro Ala Val Leu Arg Ile Leu Glu Gly Phe Gly Tyr Arg Lys
1105                1110                1115                1120
Glu Asp Leu Arg Trp Gln Lys Thr Lys Gln Thr Gly Leu Thr Ser Trp
                1125                1130                1135
Leu Asn Ile Lys Lys Ser Gly Thr Gly Gly Gly Gly Ala Thr Val Lys
            1140                1145                1150
```

```
Phe Lys Tyr Lys Gly Glu Glu Lys Glu Val Asp Ile Ser Lys Ile Lys
        1155                1160                1165

Lys Val Trp Arg Val Gly Pro Met Ile Ser Phe Thr Tyr Asp Glu Gly
        1170                1175                1180

Gly Gly Lys Thr Gly Arg Gly Ala Val Ser Glu Lys Asp Ala Pro Lys
1185                1190                1195                1200

Glu Leu Leu Gln Met Leu Glu Lys Gln Lys Ala Ala Ala Leu Glu His
                1205                1210                1215

His His His His His
                1220

<210> SEQ ID NO 4
<211> LENGTH: 1096
<212> TYPE: PRT
<213> ORGANISM: Artificial Sequence
<220> FEATURE:
<223> OTHER INFORMATION: synthetic full length Da FEN1-polymerase (USD
      minus)-Sso7d fusion DNA polymerase, fusion protein #4, Archaeon
      Desulfurococcus amylolyticus flap endonuclease (Pfu FEN1)
      without uracil sensing domain (USD) fused to Sso7d

<400> SEQUENCE: 4

Met Gly Val Asp Leu Lys Asp Ile Ile Pro Gly Glu Ala Lys Thr Val
1               5                   10                  15

Ile Glu Asp Leu Arg Ile Leu His Gly Lys Ile Val Ile Asp Gly
        20                  25                  30

Tyr Asn Ala Leu Tyr Gln Phe Leu Ala Ala Ile Arg Gln Pro Asp Gly
            35                  40                  45

Thr Pro Leu Met Asp Asn Asn Gly Arg Ile Thr Ser His Leu Ser Gly
    50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
            100                 105                 110

Val Gln Ser Gly Asp Leu Glu Leu Ala Arg Arg Tyr Ala Met Met Ser
        115                 120                 125

Ala Lys Leu Thr Glu Glu Met Val Arg Asp Ala Lys Ser Leu Leu Asp
    130                 135                 140

Ala Met Gly Ile Pro Trp Val Gln Ala Pro Ala Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
        195                 200                 205

Val Lys Pro Glu Leu Ile Glu Leu Asp Lys Leu Leu Val Gln Leu Gly
    210                 215                 220

Ile Thr Leu Glu Asn Leu Ile Asp Ile Gly Ile Leu Leu Gly Thr Asp
225                 230                 235                 240

Tyr Asn Pro Asp Gly Phe Glu Gly Ile Gly Pro Lys Lys Ala Leu Gln
                245                 250                 255

Leu Val Lys Ala Tyr Gly Gly Ile Glu Lys Ile Pro Lys Pro Ile Leu
            260                 265                 270
```

```
Lys Ser Pro Ile Glu Val Asp Val Ile Ala Ile Lys Lys Tyr Phe Leu
        275                 280                 285

Gln Pro Gln Val Thr Asp Asn Tyr Arg Ile Glu Trp His Thr Pro Asp
    290                 295                 300

Pro Asp Ala Val Lys Arg Ile Leu Val Asp Glu His Asp Phe Ser Ile
305                 310                 315                 320

Asp Arg Val Ser Thr Ala Leu Glu Arg Tyr Val Lys Ala Phe Lys Glu
                325                 330                 335

Asn Ile Arg Gly Glu Gln Lys Gly Leu Ser Lys Trp Phe Ser Lys Pro
                340                 345                 350

Lys Ser Gly Gly Ser Gly Gly Gly Ser Gly Gly Gly Ser
        355                 360                 365

Ile Pro Met Glu Gly Asp Glu Glu Leu Lys Leu Leu Ala Phe Ala Ile
        370                 375                 380

Ala Thr Leu Tyr His Glu Gly Glu Phe Gly Lys Gly Pro Ile Ile
385                 390                 395                 400

Met Ile Ser Tyr Ala Asp Glu Glu Ala Lys Val Ile Thr Trp Lys
                405                 410                 415

Lys Ile Asp Leu Pro Tyr Val Glu Val Ser Ser Glu Arg Glu Met
        420                 425                 430

Ile Lys Arg Phe Leu Lys Ile Ile Arg Glu Lys Asp Pro Asp Ile Ile
        435                 440                 445

Ile Thr Tyr Asn Gly Asp Ser Phe Asp Leu Pro Tyr Leu Ala Lys Arg
        450                 455                 460

Ala Glu Lys Leu Gly Ile Lys Leu Thr Ile Gly Arg Asp Gly Ser Glu
465                 470                 475                 480

Pro Lys Met Gln Arg Ile Gly Asp Met Thr Ala Val Glu Val Lys Gly
                485                 490                 495

Arg Ile His Phe Asp Leu Tyr His Val Ile Arg Arg Thr Ile Asn Leu
                500                 505                 510

Pro Thr Tyr Thr Leu Glu Ala Val Tyr Glu Ala Ile Phe Gly Lys Pro
        515                 520                 525

Lys Glu Lys Val Tyr Ala Asp Glu Ile Ala Lys Ala Trp Glu Thr Gly
        530                 535                 540

Glu Gly Leu Glu Arg Val Ala Lys Tyr Ser Met Glu Asp Ala Lys Ala
545                 550                 555                 560

Thr Tyr Glu Leu Gly Lys Glu Phe Phe Pro Met Glu Ala Gln Leu Ser
                565                 570                 575

Arg Leu Val Gly Gln Pro Leu Trp Asp Val Ser Arg Ser Ser Thr Gly
                580                 585                 590

Asn Leu Val Glu Trp Phe Leu Leu Arg Lys Ala Tyr Glu Arg Asn Glu
        595                 600                 605

Leu Ala Pro Asn Lys Pro Asp Glu Arg Glu Tyr Glu Arg Arg Leu Arg
610                 615                 620

Glu Ser Tyr Ala Gly Gly Phe Val Lys Glu Pro Lys Gly Leu Trp
625                 630                 635                 640

Glu Asn Ile Val Ser Leu Asp Phe Arg Ala Leu Tyr Pro Ser Ile Ile
                645                 650                 655

Ile Thr His Asn Val Ser Pro Asp Thr Leu Asn Arg Glu Gly Cys Arg
                660                 665                 670

Asn Tyr Asp Val Ala Pro Glu Val Gly His Lys Phe Cys Lys Asp Phe
                675                 680                 685
```

```
Pro Gly Phe Ile Pro Ser Leu Leu Lys Arg Leu Leu Asp Glu Arg Gln
        690                 695                 700
Lys Ile Lys Thr Lys Met Lys Ala Ser Gln Asp Pro Ile Glu Lys Ile
705                 710                 715                 720
Met Leu Asp Tyr Arg Gln Arg Ala Ile Lys Ile Leu Ala Asn Ser Tyr
                725                 730                 735
Tyr Gly Tyr Tyr Gly Tyr Ala Lys Ala Arg Trp Tyr Cys Lys Glu Cys
                740                 745                 750
Ala Glu Ser Val Thr Ala Trp Gly Arg Glu Tyr Ile Glu Phe Val Trp
            755                 760                 765
Lys Glu Leu Glu Glu Lys Phe Gly Phe Lys Val Leu Tyr Ile Asp Thr
770                 775                 780
Asp Gly Leu Tyr Ala Thr Ile Pro Gly Gly Lys Ser Glu Glu Ile Lys
785                 790                 795                 800
Lys Lys Ala Leu Glu Phe Val Asp Tyr Ile Asn Ala Lys Leu Pro Gly
                805                 810                 815
Leu Leu Glu Leu Glu Tyr Glu Gly Phe Tyr Lys Arg Gly Phe Phe Val
                820                 825                 830
Thr Lys Lys Lys Tyr Ala Leu Ile Asp Glu Glu Gly Lys Ile Ile Thr
        835                 840                 845
Arg Gly Leu Glu Ile Val Arg Arg Asp Trp Ser Glu Ile Ala Lys Glu
850                 855                 860
Thr Gln Ala Arg Val Leu Glu Ala Ile Leu Lys His Gly Asn Val Glu
865                 870                 875                 880
Glu Ala Val Arg Ile Val Lys Glu Val Thr Gln Lys Leu Ser Lys Tyr
                885                 890                 895
Glu Ile Pro Pro Glu Lys Leu Ala Ile Tyr Glu Gln Ile Thr Arg Pro
                900                 905                 910
Leu His Glu Tyr Lys Ala Ile Gly Pro His Val Ala Val Ala Lys Arg
        915                 920                 925
Leu Ala Ala Lys Gly Val Lys Ile Lys Pro Gly Met Val Ile Gly Tyr
        930                 935                 940
Ile Val Leu Arg Gly Asp Gly Pro Ile Ser Asn Arg Ala Ile Leu Ala
945                 950                 955                 960
Glu Glu Tyr Asp Pro Arg Lys His Lys Tyr Asp Ala Glu Tyr Tyr Ile
                965                 970                 975
Glu Asn Gln Val Leu Pro Ala Val Leu Arg Ile Leu Glu Gly Phe Gly
            980                 985                 990
Tyr Arg Lys Glu Asp Leu Arg Trp Gln Lys Thr Lys Gln Thr Gly Leu
        995                 1000                1005
Thr Ser Trp Leu Asn Ile Lys Lys Ser Gly Thr Gly Gly Gly Gly Ala
1010                1015                1020
Thr Val Lys Phe Lys Tyr Lys Gly Glu Glu Lys Glu Val Asp Ile Ser
1025                1030                1035                1040
Lys Ile Lys Lys Val Trp Arg Val Gly Pro Met Ile Ser Phe Thr Tyr
                1045                1050                1055
Asp Glu Gly Gly Gly Lys Thr Gly Arg Gly Ala Val Ser Glu Lys Asp
                1060                1065                1070
Ala Pro Lys Glu Leu Leu Gln Met Leu Glu Lys Gln Lys Ala Ala Ala
            1075                1080                1085
Leu Glu His His His His His His
        1090                1095
```

<210> SEQ ID NO 5
<211> LENGTH: 3602
<212> TYPE: DNA
<213> ORGANISM: Artificial Sequence
<220> FEATURE:
<223> OTHER INFORMATION: synthetic full length codon-optimized Pfu
      FEN1-polymerase-Sso7d fusion DNA polymerase, fusion protein #1,
      Archaeon Pyrococcus furiosus flap endonuclease (Pfu FEN1) fused to
      Sulfolobus solfataricus Sso7d

<400> SEQUENCE: 5

| | |
|---|---|
| atgggcgtgc cgatcggtga atcatccca cgtaaagaaa tcgagctgga gaacctgtac | 60 |
| ggtaaaaaaa ttgctatcga cgctctcaac gccatttacc agttcctgtc aactatccgt | 120 |
| cagaaagacg gcactccgct catggatagc aagggtcgta ttacctctca cctgtccggc | 180 |
| ctgttctacc gtacgatcaa tctgatggaa gcaggggatta aaccggtcta tgtgttcgat | 240 |
| ggcgaaccgc cagagttcaa aagaaagag ttggaaaaac gccgtgaagc acgtgaagaa | 300 |
| gcggaagaaa atggcgtga agctctggaa aaggcgaaa tcgaagaagc gcgtaaatac | 360 |
| gcccagcgtg cgacccgtgt caatgaaatg ctgatcgaag acgccaaaaa actgctggaa | 420 |
| ttgatgggta tccctatcgt gcaggctcca tctgaaggcg aagctcaagc ggcgtatatg | 480 |
| gccgcaaaag gctctgttta tgcgtctgct tcccaagatt acgactccct gctgtttggt | 540 |
| gcaccgcgcc tggtgcgtaa cctgaccatc acgggtaagc gtaagttgcc gggtaagaac | 600 |
| gtttatgtgg aaattaaacc tgaactgatt attctggaag aggtcctgaa agagctgaaa | 660 |
| ctgacacgcg aaaaactgat tgaactggct atcctggttg cacagactaa caccccaggc | 720 |
| ggtatcaaag catcggtct gaaaaaagcg cttgaaatcg tgcgtcacag taagatccgg | 780 |
| ctggctaagt ttcagaaaca gagcgacgtg gacctgtatg caattaaaga gttcttcctg | 840 |
| aaccctccgg ttactgataa ctacaacctg gtttggcgcg atccagacga ggagggtatc | 900 |
| ctgaaatttc tgtgtgatga acacgatttc tccgaggaac gtgttaaaaa cggtctggag | 960 |
| cgtctgaaga aggcgatcaa atctggcggt ggtagcggtg cggcggttc tggcggtggt | 1020 |
| ggcagcatcc tggatgctga ctacatcact gaagaaggca accggttat ccgtctgttc | 1080 |
| aaaaaagaga acggcgaatt taagattgag catgatcgca cctttcgtcc atacatttac | 1140 |
| gctctgctga agatgattc taagattgag gaagttaaaa aaatcactgc tgagcgccat | 1200 |
| ggcaagattg ttcgtatcgt tgatgcggaa aaggtagaaa agaaatttct gggcagacca | 1260 |
| atcaccgtgt ggagactgta tttcgaacat ccacaagatg ttccgactat cgcgagaaa | 1320 |
| attcgcgaac attctgcagt tgttgacatc ttcgaatacg atattccatt tgcaaagcgt | 1380 |
| tacctcatcg acaaaggcct gataccaatg gagggcgatg aagaactcaa gctcctggcg | 1440 |
| ttcgctatag caaccctcta tcacgaaggc gaagagtttg gtaaaggccc aattataatg | 1500 |
| atcagctatg cagatgaaga agaagcaaag gtgattactt ggaaaaaaat agatctccca | 1560 |
| tacgttgagg ttgtatcttc cgagcgcgag atgattaagc gctttctcaa aattatccgc | 1620 |
| gagaaggatc cggacattat cattacttat aacggcgact ttttgaccct cccatatctg | 1680 |
| gcgaaacgcg cagaaaaact cggtattaaa ctgactatcg gccgtgatgg ttccgagccg | 1740 |
| aagatgcagc gtatcggcga tatgaccgct gtagaagtta aaggtcgtat ccatttcgac | 1800 |
| ctgtatcatg taattcgtcg tactattaac ctcccgactt acactctcga ggctgtatat | 1860 |
| gaagcaattt ttggtaagcc gaaggagaag gtatacgccg atgagattgc aaaggcgtgg | 1920 |
| gaaaccggtg agggcctcga gcgtgttgca aaatactcca tggaagatgc aaaggcgact | 1980 |
| tatgaactcg gcaaagaatt cttcccaatg gaagctcagc tctctcgcct ggttggccaa | 2040 |

```
ccactgtggg atgtttctcg ttcttccacc ggtaacctcg tagagtggtt tctcctgcgc    2100
aaagcgtacg aacgcaacga actggctccg aacaagccag atgaacgtga gtatgaacgc    2160
cgtctccgcg agtcttacgc tggtggcttt gttaaagagc cagaaaaggg cctctgggaa    2220
aacatcgtgt ccctcgattt cgcgctctg tatccgtcta ttatcattac ccacaacgtg    2280
tctccggata ctctcaaccg cgagggctgc agaaactatg atgttgctcc ggaagtaggc    2340
cacaagttct gcaaggactt cccgggcttt attccgtctc tcctgaaacg tctgctcgat    2400
gaacgccaaa agattaagac taaaatgaag gcgtcccagg atccgattga aaaataatg    2460 ctcgactatc gccaagagc gattaaaatc ctcgcaaact cttattacgg ctattatggc    2520
tatgcaaaag cacgctggta ctgtaaggag tgtgctgagt ccgttactgc ttggggtcgc    2580
gaatacatcg agttcgtgtg gaaggagctc gaagaaaagt ttggctttaa agttctctac    2640
attgacactg atggtctcta tgcgactatt ccgggtggta agtctgagga aattaagaaa    2700
aaggctctag aatttgtgga ttacattaac gcgaagctcc cggtctcct ggagctcgaa    2760 tatgaaggct tttataaacg cggcttcttc gttaccaaga gaaatatgc gctgattgat    2820 gaagaaggca aaattattac tcgtggtctc gagattgtgc ccgtgattg gagcgaaatt    2880 gcgaaagaaa ctcaagctag agttctcgag gctattctca acacggcaa cgttgaagaa    2940 gctgtgagaa ttgtaaagaa agtaacccaa aagctctcta atatgaaat ccgccagag    3000 aagctcgcga tttatgagca gattactcgc ccgctgcatg agtataaggc gattggtccg    3060
cacgtggctg ttgcaaagag actggctgct aaaggcgtga aaattaaacc gggtatggta    3120
attggctaca ttgtactccg cggcgatggt ccgattagca accgtgcaat tctagctgag    3180
gaatacgatc cgagaaagca caagtatgac gcagaatatt acattgagaa ccaggtgctc    3240
ccggcggtac tccgtattct ggagggtttt ggctaccgta aggaagacct ccgctggcaa    3300
aagactaaac agactggcct cacttcttgg ctcaacatta aaaatccgg taccggcggt    3360 ggcggtgcaa ccgtaaagtt caagtacaaa ggcgaagaaa agaggtaga catctccaag    3420 atcaagaaag tatggcgtgt gggcccaatg atctccttca cctacgacga gggcggtggc    3480
aagaccggcc gtggtgcggt aagcgaaaag gacgcgccga aggagctgct gcagatgctg    3540
gagaagcaga agcggccgc actcgagcac caccaccac accactgaga tccggctgct    3600
aa                                                                  3602
```

<210> SEQ ID NO 6
<211> LENGTH: 3227
<212> TYPE: DNA
<213> ORGANISM: Artificial Sequence
<220> FEATURE:
<223> OTHER INFORMATION: synthetic full length codon-optimized Da
    FEN1-polymerase-Sso7d fusion DNA polymerase, fusion protein #2,
    Archaeon Desulfurococcus amylolyticus flap endonuclease (Da FEN1)
    fused to Sulfolobus solfataricus Sso7d

<400> SEQUENCE: 6

```
atgggcgtgc cgatcggtga atcatccca cgtaaagaaa tcgagctgga gaacctgtac      60
ggtaaaaaaa ttgctatcga cgctctcaac gccatttacc agttcctgtc aactatccgt     120
cagaaagacg gcactccgct catggatagc aagggtcgta ttacctctca cctgtccggc     180
ctgttctacc gtacgatcaa tctgatggaa gcaggatta aaccggtcta tgtgttcgat     240
ggcgaaccgc cagagttcaa aaagaaagag ttggaaaaac gccgtgaagc acgtgaagaa     300
gcggaagaaa atggcgtga agctctggaa aaaggcgaaa tcgaagaagc gcgtaaatac     360
```

```
gcccagcgtg cgacccgtgt caatgaaatg ctgatcgaag acgccaaaaa actgctggaa    420
ttgatgggta tccctatcgt gcaggctcca tctgaaggcg aagctcaagc ggcgtatatg    480
gccgcaaaag gctctgttta tgcgtctgct tcccaagatt acgactccct gctgtttggt    540
gcaccgcgcc tggtgcgtaa cctgaccatc acgggtaagc gtaagttgcc gggtaagaac    600
gtttatgtgg aaattaaacc tgaactgatt attctggaag aggtcctgaa agagctgaaa    660
ctgacacgcg aaaaactgat tgaactggct atcctggttg gcacagacta caacccaggc    720
ggtatcaaag gcatcggtct gaaaaagcg cttgaaatcg tgcgtcacag taaagatccg    780
ctggctaagt ttcagaaaca gagcgacgtg gacctgtatg caattaaaga gttcttcctg    840
aaccctccgg ttactgataa ctacaacctg gtttggcgcg atccagacga ggagggtatc    900
ctgaaatttc tgtgtgatga acacgatttc tccgaggaac gtgttaaaaa cggtctggag    960
cgtctgaaga aggcgatcaa atctggcggt ggtagcggtg gcggcggttc tggcggtggt   1020
ggcagcatac caatggaggg cgatgaagaa ctcaagctcc tggcgttcgc tatagcaacc   1080
ctctatcacg aaggcgaaga gtttggtaaa ggcccaatta taatgatcag ctatgcagat   1140
gaagaagaag caaaggtgat tacttggaaa aaaatagatc tcccatacgt tgaggttgta   1200
tcttccgagc gcgagatgat taagcgcttt ctcaaaatta ccgcgagaa ggatccggac   1260 attatcatta cttataacgg cgactctttt gacctcccat atctggcgaa acgcgcagaa   1320
aaactcggta ttaaactgac tatcggccgt gatggttccg agccgaagat gcagcgtatc   1380
ggcgatatga ccgctgtaga agttaagggt cgtatccatt cgacctgta tcatgtaatt   1440 cgtcgtacta ttaacctccc gacttacact ctcgaggctg tatatgaagc aattttggt   1500 aagccgaagg agaaggtata cgccgatgag attgcaaagg cgtgggaaac cggtgagggc   1560
ctcgagcgtg ttgcaaaata ctccatggaa gatgcaaagg cgacttatga actcggcaaa   1620
gaattcttcc caatggaagc tcagctctct cgcctggttg ccaaccact gtgggatgtt   1680 tctcgttctt ccaccggtaa cctcgtagag tggtttctcc tgcgcaaagc gtacgaacgc   1740
aacgaactgg ctccgaacaa gccagatgaa cgtgagtatg aacgccgtct ccgcgagtct   1800
tacgctggtg gctttgttaa agagccagaa aagggcctct gggaaaacat cgtgtccctc   1860
gattttcgcg ctctgtatcc gtctattatc attacccaca acgtgtctcc ggatactctc   1920
aaccgcgagg gctgcagaaa ctatgatgtt gctccggaag taggccacaa gttctgcaag   1980
gacttcccgg gctttattcc gtctctcctg aaacgtctgc tcgatgaacg ccaaaagatt   2040
aagactaaaa tgaaggcgtc ccaggatccg attgaaaaaa taatgctcga ctatcgccaa   2100
agagcgatta aaatcctcgc aaactcttat tacggctatt atggctatgc aaaagcacgc   2160
tggtactgta aggagtgtgc tgagtccgtt actgcttggg gtcgcgaata catcgagttc   2220
gtgtggaagg agctcgaaga aaagtttggc tttaaagttc tctacattga cactgatggt   2280
ctctatgcga ctattccggg tggtaagtct gaggaaatta gaaaaaggc tctagaattt   2340 gtggattaca ttaacgcgaa gctcccgggt ctcctggagc tcgaatatga aggcttttat   2400
aaacgcggct tcttcgttac caagaagaaa tatgcgctga ttgatgaaga aggcaaaatt   2460
attactcgtg tctcgagat tgtgcgccgt gattggagcg aaattgcgaa agaaactcaa   2520
gctagagttc tcgaggctat tctcaaacac ggcaacgttg aagaagctgt gagaattgta   2580
aaagaagtaa cccaaaagct ctctaaatat gaaattccgc cagagaagct cgcgatttat   2640
gagcagatta ctcgcccgct gcatgagtat aaggcgattg gtccgcacgt ggctgttgca   2700
```

```
aagagactgg ctgctaaagg cgtgaaaatt aaaccgggta tggtaattgg ctacattgta      2760
ctccgcggcg atggtccgat tagcaaccgt gcaattctag ctgaggaata cgatccgaga      2820
aagcacaagt atgacgcaga atattacatt gagaaccagg tgctcccggc ggtactccgt      2880
attctggagg gttttggcta ccgtaaggaa gacctccgct ggcaaaagac taaacagact      2940
ggcctcactt cttggctcaa cattaaaaaa tccggtaccg gcggtggcgg tgcaaccgta      3000
aagttcaagt acaaaggcga agaaaaagag gtagacatct ccaagatcaa gaaagtatgg      3060
cgtgtgggcc caatgatctc cttcacctac gacgagggcg gtggcaagac cggccgtggt      3120
gcggtaagcg aaaaggacgc gccgaaggag ctgctgcaga tgctggagaa gcagaaagcg      3180
gccgcactcg agcaccacca ccaccaccac tgagatccgg ctgctaa                   3227
```

<210> SEQ ID NO 7
<211> LENGTH: 3680
<212> TYPE: DNA
<213> ORGANISM: Artificial Sequence
<220> FEATURE:
<223> OTHER INFORMATION: synthetic full length codon-optimized Pfu
    FEN1-polymerase (USD minus)-Sso7d fusion DNA polymerase, fusion
    protein #3, Archaeon Pyrococcus furiosus flap endonuclease (Pfu
    FEN1) without uracil sensing domain (USD) fused to Sulfolobus
    solfataricus Sso7d

<400> SEQUENCE: 7

```
atgggtgtag acctgaaaga cattatcccg ggtgaggcga agactgtgat cgaagacctg        60
cgtatcctgc acggtaagat cattgtcatt gacggttata cgcgctgta tcagttcctg        120 gctgctatcc gccaaccgga cggtactccg ctgatggata caacggtcg tattaccagc        180 catctgtctg gtctcttttta tcgtaccatc aacatcgttg aagcgggtat caaaccagta       240
tatgtatttg atggtaaacc gccggaactg aaagcgcgcg aaattgagcg tcgtaaagcc       300 gttaagaag aagccgcgaa aagtatgaa gaagcagttc agtcgggtga tcttgaactg         360
gcgcgccgtt acgccatgat gagcgcgaaa ctgacagagg aaatggttcg tgacgcgaaa       420
tctctgctgg atgcgatggg catcccgtgg gtacaggccc cggctgaagg cgaggcgcag       480
gctgcgtata tcgttaaaaa aggtgacgct tacgcttccg cttcccagga ctatgattct       540
ctgctgttcg gttcgccgaa actggtgcgt aaccttacca tctctggccg tcgtaagctg      600
ccacgtaaga cgaatacgt ggaagtaaag ccggaactga ttgaactgga taaactgcta       660
gtccagctgg gcatcaccct ggaaaacctg atcgacatcg tattctgct ggggacggat        720 tacaacccgg atggcttcga aggtatcggt ccaaaaaaag cactgcagct ggtgaaagcc       780
tatggtggca ttgaaaaaat cccgaaaccg atcctgaaat ccccgatcga agttgacgtt      840
attgctatca aaaatattt tctgcagccg caggttaccg acaactatcg catcgaatgg       900
cacaccccgg acccggatgc cgtcaaacgt atcctggtcg acgaacatga cttttccatc     960
gaccgtgtat cgacggcgct ggaacgctac gtaaaagcgt tcaaagaaaa cattcgtggt     1020
gaacagaaag gcctgtctaa gtggttctcc aagccgaaat ctggcggtgg tagcggtggc     1080
ggcggttctg gcgtggtgg cagcatcctg gatgctgact acatcactga gaaggcaaa      1140 ccggttatcc gtctgttcaa aaaagagaac ggcgaattta agattgagca tgatcgcacc     1200
tttcgtccat acatttacgc tctgctgaaa gatgattcta gattgagga agttaaaaaa     1260 atcactgctg agcgccatgg caagattgtt cgtatcgttg atgcggaaaa ggtagaaaag     1320
aaatttctgg gcagaccaat caccgtgtgg agactgtatt cgaacatcc acaagatgtt     1380 ccgactattc gcgagaaat tcgcgaacat tctgcagttg ttgacatctt cgaatacgat     1440
```

```
attccatttg caaagcgtta cctcatcgac aaaggcctga taccaatgga gggcgatgaa    1500
gaactcaagc tcctggcgtt cgctatagca accctctatc acgaaggcga agagtttggt    1560
aaaggcccaa ttataatgat cagctatgca gatgaagaag aagcaaaggt gattacttgg    1620
aaaaaaatag atctcccata cgttgaggtt gtatcttccg agcgcgagat gattaagcgc    1680
tttctcaaaa ttatccgcga gaaggatccg gacattatca ttacttataa cggcgactct    1740
tttgacctcc catatctggc gaaacgcgca gaaaaactcg gtattaaact gactatcggc    1800
cgtgatggtt ccgagccgaa gatgcagcgt atcggcgata tgaccgctgt agaagttaag    1860
ggtcgtatcc atttcgacct gtatcatgta attcgtcgta ctattaaccct cccgacttac    1920 actctcgagg ctgtatatga agcaattttt ggtaagccga aggagaaggt atacgccgat    1980
gagattgcaa aggcgtggga aaccggtgag ggcctcgagc gtgttgcaaa atactccatg    2040
gaagatgcaa aggcgactta tgaactcggc aaagaattct cccaatggga agctcagctc    2100
tctcgcctgg ttggccaacc actgtgggat gtttctcgtt cttccaccgg taacctcgta    2160
gagtggtttc tcctgcgcaa agcgtacgaa cgcaacgaac tggctccgaa caagccagat    2220
gaacgtgagt atgaacgccg ctccgcgagt cttacgctg gtggctttgt taaagagcca    2280
gaaaagggcc tctgggaaaa catcgtgtcc ctcgattttc gcgctctgta tccgtctatt    2340
atcattaccc acaacgtgtc tccggatact ctcaaccgcg agggctgcag aaactatgat    2400
gttgctccgg aagtaggcca caagttctgc aaggacttcc cgggctttat tccgtctctc    2460
ctgaaacgtc tgctcgatga acgccaaaag attaagacta aaatgaaggc gtcccaggat    2520
ccgattgaaa aataatgct cgactatcgc caaagagcga ttaaaatcct cgcaaactct    2580
tattacggct attatggcta tgcaaaagca cgctggtact gtaaggagtg tgctgagtcc    2640
gttactgctt ggggtcgcga atacatcgag ttcgtgtgga aggagctcga agaaaagttt    2700
ggctttaaag ttctctacat tgacactgat ggtctctatg cgactattcc gggtggtaag    2760
tctgaggaaa ttaagaaaaa ggctctagaa tttgtggatt acattaacgc gaagctcccg    2820
ggtctcctgg agctcgaata tgaaggcttt tataaacgcg gcttcttcgt taccaagaag    2880
aaatatgcgc tgattgatga agaaggcaaa attattactc gtggtctcga gattgtgcgc    2940
cgtgattgga gcgaaattgc gaaagaaact caagctagag ttctcgaggc tattctcaaa    3000
cacggcaacg ttgaagaagc tgtgagaatt gtaaagaag taacccaaaa gctctctaaa    3060
tatgaaattc cgccagagaa gctcgcgatt tatgagcaga ttactcgccc gctgcatgag    3120
tataaggcga ttggtccgca cgtggctgtt gcaaagagac tggctgctaa aggcgtgaaa    3180
attaaaccgg gtatggtaat tggctacatt gtactccgcg gcgatggtcc gattagcaac    3240
cgtgcaattc tagctgagga atacgatccg agaaagcaca gtatgacgc agaatattac    3300 attgagaacc aggtgctccc ggcggtactc cgtattctgg agggttttgg ctaccgtaag    3360
gaagacctcc gctggcaaaa gactaaacag actggcctca cttcttggct caacattaaa    3420
aaatccggta ccggcggtgg cggtgcaacc gtaaagttca agtacaaagg cgaagaaaaa    3480
gaggtagaca tctccaagat caagaaagta tggcgtgtgg gcccaatgat ctccttcacc    3540
tacgacgagg gcgtggcaa gaccggccgt ggtgcgtaa gcgaaaagga cgcgccgaag    3600
gagctgctgc agatgctgga gaagcagaaa gcggccgcac tcgagcacca ccaccaccac    3660
cactgagatc cggctgctaa                                              3680
```

<210> SEQ ID NO 8

<211> LENGTH: 3305
<212> TYPE: DNA
<213> ORGANISM: Artificial Sequence
<220> FEATURE:
<223> OTHER INFORMATION: synthetic full length codon-optimized Da
    FEN1-polymerase (USD minus)-Sso7d fusion DNA polymerase, fusion
    protein #4, Archaeon Desulfurococcus amylolyticus flap
    endonuclease (Da FEN1) without uracil sensing domain (USD) fused
    to Sso7d

<400> SEQUENCE: 8

```
atgggtgtag acctgaaaga cattatcccg ggtgaggcga agactgtgat cgaagacctg      60
cgtatcctgc acggtaagat cattgtcatt gacggttata cgcgctgta tcagttcctg     120 gctgctatcc gccaaccgga cggtactccg ctgatggata caacggtcg tattaccagc     180 catctgtctg gtctctttta tcgtaccatc aacatcgttg aagcgggtat caaaccagta     240
tatgtatttg atggtaaacc gccggaactg aaagcgcgcg aaattgagcg tcgtaaagcc     300
gttaaagaag aagccgcgaa aaagtatgaa gaagcagttc agtcgggtga tcttgaactg     360
gcgcgccgtt acgccatgat gagcgcgaaa ctgacagagg aaatggttcg tgacgcgaaa     420
tctctgctgg atgcgatggg catcccgtgg gtacaggccc cggctgaagg cgaggcgcag     480
gctgcgtata tcgttaaaaa aggtgacgct tacgcttccg cttcccagga ctatgattct     540
ctgctgttcg gttcgccgaa actggtgcgt aaccttacca tctctggccg tcgtaagctg     600
ccacgtaaga acgaatacgt ggaagtaaag ccggaactga ttgaactgga taaactgcta     660
gtccagctgg gcatcaccct ggaaaacctg atcgacatcg gtattctgct ggggacggat     720
tacaacccgg atgcttcga aggtatcggt ccaaaaaag cactgcagct ggtgaaagcc     780
tatggtggca ttgaaaaaat cccgaaaccg atcctgaaat ccccgatcga agttgacgtt     840
attgctatca aaaaatattt tctgcagccg caggttaccg acaactatcg catcgaatgg     900
cacaccccgg accccggatgc cgtcaaacgt atcctggtcg acgaacatga cttttccatc     960
gaccgtgtat cgacggcgct ggaacgctac gtaaaagcgt tcaaagaaaa cattcgtggt    1020
gaacagaaag gcctgtctaa gtggttctcc aagccgaaat ctggcggtgg tagcggtggc    1080
ggcggttctg gcggtggtgg cagcatacca atggagggcg atgaagaact caagctcctg    1140
gcgttcgcta tagcaaccct ctatcacgaa ggcgaagagt ttggtaaagg cccaattata    1200
atgatcagct atgcagatga agaagaagca aaggtgatta cttggaaaaa aatagatctc    1260
ccatacgttg aggttgtatc ttccgagcgc gagatgatta gcgctttct caaaattatc    1320 cgcgagaagg atccggacat tatcattact tataacggcg actctttga cctcccatat    1380 ctggcgaaac gcgcagaaaa actcggtatt aaactgacta tcggccgtga tggttccgag    1440
ccgaagatgc agcgtatcgg cgatatgacc gctgtagaag ttaagggtcg tatccatttc    1500
gacctgtatc atgtaattcg tcgtactatt aacctcccga cttacactct cgaggctgta    1560
tatgaagcaa tttttggtaa gccgaaggag aaggtatacg ccgatgagat tgcaaaggcg    1620
tgggaaaccg gtgagggcct cgagcgtgtt gcaaaatact ccatggaaga tgcaaaggcg    1680
acttatgaac tcggcaaaga attcttccca atggaagctc agctctctcg cctggttggc    1740
caaccactgt gggatgtttc tcgttcttcc accggtaacc tcgtagagtg gtttctcctg    1800
cgcaaagcgt acgaacgcaa cgaactggct ccgaacaagc cagatgaacg tgagtatgaa    1860
cgccgtctcc gcgagtctta cgctggtggc tttgttaaag agccagaaaa gggcctctgg    1920
gaaaacatcg tgtccctcga ttttcgcgct ctgtatccgt ctattatcat tacccacaac    1980
gtgtctccgg atactctcaa ccgcgagggc tgcagaaact atgatgttgc tccggaagta    2040
```

```
ggccacaagt tctgcaagga cttcccgggc tttattccgt ctctcctgaa acgtctgctc    2100
gatgaacgcc aaaagattaa gactaaaatg aaggcgtccc aggatccgat tgaaaaaata    2160
atgctcgact atcgccaaag agcgattaaa atcctcgcaa actcttatta cggctattat    2220
ggctatgcaa aagcacgctg gtactgtaag gagtgtgctg agtccgttac tgcttggggt    2280
cgcgaataca tcgagttcgt gtggaaggag ctcgaagaaa agtttggctt taaagttctc    2340
tacattgaca ctgatggtct ctatgcgact attccgggtg gtaagtctga ggaaattaag    2400
aaaaaggctc tagaatttgt ggattacatt aacgcgaagc tcccgggtct cctggagctc    2460
gaatatgaag ctttttataa acgcggcttc ttcgttacca agaagaaata tgcgctgatt    2520
gatgaagaag gcaaaattat tactcgtggt ctcgagattg tgcgccgtga ttggagcgaa    2580
attgcgaaag aaactcaagc tagagttctc gaggctattc tcaaacacgg caacgttgaa    2640
gaagctgtga gaattgtaaa agaagtaacc caaaagctct ctaaatatga aattccgcca    2700
gagaagctcg cgatttatga gcagattact cgcccgctgc atgagtataa ggcgattggt    2760
ccgcacgtgg ctgttgcaaa gagactggct gctaaaggcg tgaaaattaa accgggtatg    2820
gtaattggct acattgtact ccgcggcgat ggtccgatta gcaaccgtgc aattctagct    2880
gaggaatacg atccgagaaa gcacaagtat gacgcagaat attacattga gaaccaggtg    2940
ctcccggcgg tactccgtat tctggagggt tttggctacc gtaaggaaga cctccgctgg    3000
caaaagacta acagactggg cctcacttct tggctcaaca ttaaaaaatc cggtaccggc    3060
ggtggcggtg caaccgtaaa gttcaagtac aaaggcgaag aaaaagaggt agacatctcc    3120
aagatcaaga agtatggcg tgtgggccca atgatctcct tcacctacga cgagggcggt    3180
ggcaagaccg gccgtggtgc ggtaagcgaa aaggacgcgc cgaaggagct gctgcagatg    3240
ctggagaagc agaaagcggc cgcactcgag caccaccacc accaccactg agatccggct    3300
gctaa                                                                3305
```

<210> SEQ ID NO 9
<211> LENGTH: 1059
<212> TYPE: DNA
<213> ORGANISM: Artificial Sequence
<220> FEATURE:
<223> OTHER INFORMATION: synthetic full length codon-optimized Da
      FEN1-polymerase (USD minus)-Sso7d fusion DNA
      polymerase, Archaeon Desulfurococcus amylolyticus
      flap endonuclease (Da FEN1)

<400> SEQUENCE: 9

```
atgggtgtag acctgaaaga cattatcccg ggtgaggcga agactgtgat cgaagacctg     60
cgtatcctgc acggtaagat cattgtcatt gacggttata cgcgctgta tcagttcctg    120
gctgctatcc gccaaccgga cggtactccg ctgatggata caacggtcg tattaccagc    180
catctgtctg gtctctttta tcgtaccatc aacatcgttg aagcgggtat caaaccagta    240
tatgtatttg atggtaaacc gccggaactg aaagcgcgcg aaattgagcg tcgtaaagcc    300
gttaaagaag aagccgcgaa aaagtatgaa gaagcagttc agtcgggtga tcttgaactg    360
gcgcgccgtt acgccatgat gagcgcgaaa ctgacagagg aaatggttcg tgacgcgaaa    420
tctctgctgg atgcgatggg catcccgtgg gtacaggccc cggctgaagg cgaggcgcag    480
gctgcgtata tcgttaaaaa aggtgacgct tacgcttccg cttcccagga ctatgattct    540
ctgctgttcg gttcgccgaa actggtgcgt aaccttacca tctctggccg tcgtaagctg    600
ccacgtaaga acgaatacgt ggaagtaaag ccggaactga ttgaactgga taaactgcta    660
```

```
gtccagctgg gcatcaccct ggaaaacctg atcgacatcg gtattctgct ggggacggat    720
tacaacccgg atggcttcga aggtatcggt ccaaaaaaag cactgcagct ggtgaaagcc    780
tatggtggca ttgaaaaaat cccgaaaccg atcctgaaat ccccgatcga agttgacgtt    840
attgctatca aaaatatttt tctgcagccg caggttaccg acaactatcg catcgaatgg    900
cacaccccgg acccggatgc cgtcaaacgt atcctggtcg acgaacatga cttttccatc    960
gaccgtgtat cgacggcgct ggaacgctac gtaaaagcgt tcaaagaaaa cattcgtggt   1020
gaacagaaag gcctgtctaa gtggttctcc aagccgaaa                          1059
```

<210> SEQ ID NO 10
<211> LENGTH: 353
<212> TYPE: PRT
<213> ORGANISM: Artificial Sequence
<220> FEATURE:
<223> OTHER INFORMATION: synthetic Da FEN1 polymerase, Archaeon
      Desulfurococcus amylolyticus flap endonuclease (Da FEN1)

<400> SEQUENCE: 10

```
Met Gly Val Asp Leu Lys Asp Ile Ile Pro Gly Glu Ala Lys Thr Val
 1               5                  10                  15

Ile Glu Asp Leu Arg Ile Leu His Gly Lys Ile Val Ile Asp Gly
            20                  25                  30

Tyr Asn Ala Leu Tyr Gln Phe Leu Ala Ala Ile Arg Gln Pro Asp Gly
        35                  40                  45

Thr Pro Leu Met Asp Asn Asn Gly Arg Ile Thr Ser His Leu Ser Gly
    50                  55                  60

Leu Phe Tyr Arg Thr Ile Asn Ile Val Glu Ala Gly Ile Lys Pro Val
65                  70                  75                  80

Tyr Val Phe Asp Gly Lys Pro Pro Glu Leu Lys Ala Arg Glu Ile Glu
                85                  90                  95

Arg Arg Lys Ala Val Lys Glu Glu Ala Ala Lys Lys Tyr Glu Glu Ala
            100                 105                 110

Val Gln Ser Gly Asp Leu Glu Leu Ala Arg Arg Tyr Ala Met Met Ser
        115                 120                 125

Ala Lys Leu Thr Glu Glu Met Val Arg Asp Ala Lys Ser Leu Leu Asp
    130                 135                 140

Ala Met Gly Ile Pro Trp Val Gln Ala Pro Ala Glu Gly Glu Ala Gln
145                 150                 155                 160

Ala Ala Tyr Ile Val Lys Lys Gly Asp Ala Tyr Ala Ser Ala Ser Gln
                165                 170                 175

Asp Tyr Asp Ser Leu Leu Phe Gly Ser Pro Lys Leu Val Arg Asn Leu
            180                 185                 190

Thr Ile Ser Gly Arg Arg Lys Leu Pro Arg Lys Asn Glu Tyr Val Glu
        195                 200                 205

Val Lys Pro Glu Leu Ile Glu Leu Asp Lys Leu Leu Val Gln Leu Gly
    210                 215                 220

Ile Thr Leu Glu Asn Leu Ile Asp Ile Gly Ile Leu Leu Gly Thr Asp
225                 230                 235                 240

Tyr Asn Pro Asp Gly Phe Glu Gly Ile Gly Pro Lys Lys Ala Leu Gln
                245                 250                 255

Leu Val Lys Ala Tyr Gly Gly Ile Glu Lys Ile Pro Lys Pro Ile Leu
            260                 265                 270

Lys Ser Pro Ile Glu Val Asp Val Ile Ala Ile Lys Lys Tyr Phe Leu
        275                 280                 285
```

-continued

```
Gln Pro Gln Val Thr Asp Asn Tyr Arg Ile Glu Trp His Thr Pro Asp
    290                 295                 300
Pro Asp Ala Val Lys Arg Ile Leu Val Asp Glu His Asp Phe Ser Ile
305                 310                 315                 320
Asp Arg Val Ser Thr Ala Leu Glu Arg Tyr Val Lys Ala Phe Lys Glu
                325                 330                 335
Asn Ile Arg Gly Glu Gln Lys Gly Leu Ser Lys Trp Phe Ser Lys Pro
            340                 345                 350
Lys

<210> SEQ ID NO 11
<211> LENGTH: 45
<212> TYPE: DNA
<213> ORGANISM: Artificial Sequence
<220> FEATURE:
<223> OTHER INFORMATION: synthetic linker between Da FEN1 and
      Pfu/DeepVent hybrid DNA polymerase

<400> SEQUENCE: 11
tctggcggtg gtagcggtgg cggcggttct ggcggtggtg gcagc              45

<210> SEQ ID NO 12
<211> LENGTH: 15
<212> TYPE: PRT
<213> ORGANISM: Artificial Sequence
<220> FEATURE:
<223> OTHER INFORMATION: synthetic linker between Da FEN1 and
      Pfu/DeepVent hybrid DNA polymerase

<400> SEQUENCE: 12

Ser Gly Gly Gly Ser Gly Gly Gly Ser Gly Gly Gly Gly Ser
  1               5                  10                  15

<210> SEQ ID NO 13
<211> LENGTH: 357
<212> TYPE: DNA
<213> ORGANISM: Artificial Sequence
<220> FEATURE:
<223> OTHER INFORMATION: synthetic Pfu/DeepVent hybrid DNA polymerase
      uracil-sensing domain (USD)

<400> SEQUENCE: 13
atcctggatg ctgactacat cactgaagaa ggcaaaccgg ttatccgtct gttcaaaaaa     60
gagaacggcg aatttaagat tgagcatgat cgcacctttc gtccatacat ttacgctctg    120
ctgaaagatg attctaagat tgaggaagtt aaaaaaatca ctgctgagcg ccatggcaag    180
attgttcgta tcgttgatgc ggaaaaggta gaaaagaaat ttctgggcag accaatcacc    240
gtgtggagac tgtatttcga acatccacaa gatgttccga ctattcgcga gaaaattcgc    300
gaacattctg cagttgttga catcttcgaa tacgatattc catttgcaaa gcgttac      357

<210> SEQ ID NO 14
<211> LENGTH: 375
<212> TYPE: DNA
<213> ORGANISM: Artificial Sequence
<220> FEATURE:
<223> OTHER INFORMATION: synthetic Pfu/DeepVent hybrid DNA polymerase
      uracil-sensing domain (USD) plus nucleotides removed in USD minus
      construct

<400> SEQUENCE: 14
atcctggatg ctgactacat cactgaagaa ggcaaaccgg ttatccgtct gttcaaaaaa     60
```

-continued

| | |
|---|---|
| gagaacggcg aatttaagat tgagcatgat cgcaccttc gtccatacat ttacgctctg | 120 |
| ctgaaagatg attctaagat tgaggaagtt aaaaaaatca ctgctgagcg ccatggcaag | 180 |
| attgttcgta tcgttgatgc ggaaaaggta gaaaagaaat ttctgggcag accaatcacc | 240 |
| gtgtggagac tgtatttcga acatccacaa gatgttccga ctattcgcga gaaaattcgc | 300 |
| gaacattctg cagttgttga catcttcgaa tacgatattc catttgcaaa gcgttacctc | 360 |
| atcgacaaag gcctg | 375 |

<210> SEQ ID NO 15
<211> LENGTH: 1944
<212> TYPE: DNA
<213> ORGANISM: Artificial Sequence
<220> FEATURE:
<223> OTHER INFORMATION: synthetic Pfu/DeepVent hybrid DNA polymerase
      without uracil-sensing domain (USD)

<400> SEQUENCE: 15

| | |
|---|---|
| ataccaatgg agggcgatga agaactcaag ctcctggcgt tcgctatagc aaccctctat | 60 |
| cacgaaggcg aagagtttgg taaaggccca attataatga tcagctatgc agatgaagaa | 120 |
| gaagcaaagg tgattacttg gaaaaaaata gatctcccat acgttgaggt tgtatcttcc | 180 |
| gagcgcgaga tgattaagcg ctttctcaaa attatccgcg agaaggatcc ggacattatc | 240 |
| attacttata acggcgactc ttttgacctc ccatatctgg cgaaacgcgc agaaaaactc | 300 |
| ggtattaaac tgactatcgg ccgtgatggt tccgagccga gatgcagcg tatcggcgat | 360 |
| atgaccgctg tagaagttaa gggtcgtatc catttcgacc tgtatcatgt aattcgtcgt | 420 |
| actattaacc tcccgactta cactctcgag gctgtatatg aagcaatttt tggtaagccg | 480 |
| aaggagaagg tatacgccga tgagattgca aaggcgtggg aaaccggtga gggcctcgag | 540 |
| cgtgttgcaa atactccat ggaagatgca aaggcgactt atgaactcgg caaagaattc | 600 |
| ttcccaatgg aagctcagct ctctcgcctg gttggccaac cactgtggga tgtttctcgt | 660 |
| tcttccaccg gtaacctcgt agagtggttt ctcctgcgca aagcgtacga acgcaacgaa | 720 |
| ctggctccga caagccaga tgaacgtgag tatgaacgcc gtctccgcga gtcttacgct | 780 |
| ggtggctttg ttaaagagcc agaaaagggc ctctgggaaa acatcgtgtc cctcgatttt | 840 |
| cgcgctctgt atccgtctat tatcattacc cacaacgtgt ctccggatac tctcaaccgc | 900 |
| gagggctgca gaaactatga tgttgctccg gaagtaggcc acaagttctg caaggacttc | 960 |
| ccgggcttta ttccgtctct cctgaaacgt ctgctcgatg aacgccaaaa gattaagact | 1020 |
| aaaatgaagg cgtcccagga tccgattgaa aaaataatgc tcgactatcg ccaagagcg | 1080 |
| attaaaatcc tcgcaaactc ttattacggc tattatggct atgcaaaagc acgctggtac | 1140 |
| tgtaaggagt gtgctgagtc cgttactgct tggggtcgcg aatacatcga gttcgtgtgg | 1200 |
| aaggagctcg aagaaaagtt tggctttaaa gttctctaca ttgacactga tggtctctat | 1260 |
| gcgactattc cgggtggtaa gtctgaggaa attaagaaaa aggctctaga atttgtggat | 1320 |
| tacattaacg cgaagctccc gggtctcctg gagctcgaat atgaaggctt ttataaacgc | 1380 |
| ggcttcttcg ttaccaagaa gaaatatgcg ctgattgatg aagaaggcaa aattattact | 1440 |
| cgtggtctcg agattgtgcg ccgtgattgg agcgaaattg cgaaagaaac tcaagctaga | 1500 |
| gttctcgagg ctattctcaa acacggcaac gttgaagaag ctgtgagaat tgtaaagaa | 1560 |
| gtaacccaaa agctctctaa atatgaaatt ccgccagaga gctcgcgat ttatgagcag | 1620 |
| attactcgcc cgctgcatga gtataaggcg attggtccgc acgtggctgt tgcaaagaga | 1680 |

```
ctggctgcta aaggcgtgaa aattaaaccg gtatggtaa ttggctacat tgtactccgc    1740
ggcgatggtc cgattagcaa ccgtgcaatt ctagctgagg aatacgatcc gagaaagcac   1800
aagtatgacg cagaatatta cattgagaac caggtgctcc cggcggtact ccgtattctg   1860
gagggttttg gctaccgtaa ggaagacctc cgctggcaaa agactaaaca gactggcctc   1920
acttcttggc tcaacattaa aaaa                                         1944
```

<210> SEQ ID NO 16
<211> LENGTH: 2319
<212> TYPE: DNA
<213> ORGANISM: Artificial Sequence
<220> FEATURE:
<223> OTHER INFORMATION: synthetic Pfu/DeepVent hybrid DNA polymerase
      with uracil-sensing domain (USD)

<400> SEQUENCE: 16

```
atcctggatg ctgactacat cactgaagaa ggcaaaccgg ttatccgtct gttcaaaaaa     60
gagaacggcg aatttaagat tgagcatgat cgcacctttc gtccatacat ttacgctctg    120
ctgaaagatg attctaagat tgaggaagtt aaaaaaatca ctgctgagcg ccatggcaag    180
attgttcgta tcgttgatgc ggaaaaggta gaaaagaaat ttctgggcag accaatcacc    240
gtgtggagac tgtatttcga acatccacaa gatgttccga ctattcgcga gaaaattcgc    300
gaacattctg cagttgttga catcttcgaa tacgatattc catttgcaaa agcttacctc    360
atcgacaaag gcctgataccc aatggagggc gatgaagaac tcaagctcct ggcgttcgct    420
atagcaaccc tctatcacga aggcgaagag tttggtaaag cccaattat aatgatcagc    480 tatgcagatg aagaagaagc aaaggtgatt acttggaaaa aaatagatct cccatacgtt    540
gaggttgtat cttccgagcg cgagatgatt aagcgctttc tcaaaattat ccgcgagaag    600
gatccggaca ttatcattac ttataacggc gactcttttg acctcccata tctggcgaaa    660
cgcgcagaaa actcggtat taaactgact atcggccgtg atggttccga gccgaagatg    720
cagcgtatcg gcgatatgac cgctgtagaa gttaagggtc gtatccattt cgacctgtat    780
catgtaattc gtcgtactat taacctcccg acttacactc tcgaggctgt atatgaagca    840
atttttggta agccgaagga gaaggtatac gccgatgaga ttgcaaaggc gtgggaaacc    900
ggtgagggcc tcgagcgtgt tgcaaaatac tccatggaag atgcaaaggc gacttatgaa    960
ctcggcaaag aattcttccc aatggaagct cagctctctc gcctggttgg ccaaccactg   1020
tgggatgttt ctcgttcttc caccggtaac ctcgtagagt ggtttctcct gcgcaaagcg   1080
tacgaacgca cgaactggc tccgaacaag ccagatgaac gtgagtatga cgccgtctc    1140 cgcgagtctt acgctggtgg ctttgttaaa gagccagaaa agggcctctg gaaaacatc    1200 gtgtccctcg attttcgcgc tctgtatccg tctattatca ttacccacaa cgtgtctccg    1260
gatactctca accgcgaggg ctgcagaaac tatgatgttg ctccggaagt aggccacaag   1320
ttctgcaagg acttccccgg ctttattccg tctctcctga acgtctgct cgatgaacgc    1380 caaaagatta agactaaaat gaaggcgtcc caggatccga ttgaaaaaat aatgctcgac   1440
tatcgccaaa gagcgattaa atcctcgca aactcttatt acggctatta tggctatgca    1500
aaagcacgct ggtactgtaa ggagtgtgct gagtccgtta ctgcttgggg tcgcgaatac   1560
atcgagttcg tgtggaagga gctcgaagaa aagtttggct taaagttct ctacattgac    1620 actgatggtc tctatgcgac tattccgggt ggtaagtctg aggaaattaa gaaaaggct   1680 ctagaatttg tggattacat taacgcgaag ctcccgggtc tcctggagct cgaatatgaa    1740
```

-continued

```
ggctttata  aacgcggctt  cttcgttacc  aagaagaaat  atgcgctgat  tgatgaagaa  1800
ggcaaaatta ttactcgtgg  tctcgagatt  gtgcgccgtg  attggagcga  aattgcgaaa  1860
gaaactcaag ctagagttct  cgaggctatt  ctcaaacacg  gcaacgttga  agaagctgtg  1920
agaattgtaa aagaagtaac  ccaaaagctc  tctaaatatg  aaattccgcc  agagaagctc  1980
gcgatttatg agcagattac  tcgcccgctg  catgagtata  aggcgattgg  tccgcacgtg  2040
gctgttgcaa agagactggc  tgctaaaggc  gtgaaaatta  aaccgggtat  ggtaattggc  2100
tacattgtac tccgcggcga  tggtccgatt  agcaaccgtg  caattctagc  tgaggaatac  2160
gatccgagaa agcacaagta  tgacgcagaa  tattacattg  agaaccaggt  gctcccggcg  2220
gtactccgta ttctggaggg  ttttggctac  cgtaaggaag  acctccgctg  gcaaaagact  2280
aaacagactg gcctcacttc  ttggctcaac  attaaaaaa                           2319

<210> SEQ ID NO 17
<211> LENGTH: 21
<212> TYPE: DNA
<213> ORGANISM: Artificial Sequence
<220> FEATURE:
<223> OTHER INFORMATION: synthetic linker between DNA polymerase and
      Sso7d

<400> SEQUENCE: 17
tccggtaccg gcggtggcgg t                                                21

<210> SEQ ID NO 18
<211> LENGTH: 201
<212> TYPE: DNA
<213> ORGANISM: Artificial Sequence
<220> FEATURE:
<223> OTHER INFORMATION: synthetic linker between DNA polymerase and
      Sso7d

<400> SEQUENCE: 18
gcaaccgtaa agttcaagta caaaggcgaa gaaaagagg tagacatctc caagatcaag       60
aaagtatggc gtgtgggccc aatgatctcc ttcacctacg acgagggcgg tggcaagacc      120
ggccgtggtg cggtaagcga aaaggacgcg ccgaaggagc tgctgcagat gctggagaag      180
cagaaagcgg ccgcactcga g                                                201

<210> SEQ ID NO 19
<211> LENGTH: 125
<212> TYPE: PRT
<213> ORGANISM: Artificial Sequence
<220> FEATURE:
<223> OTHER INFORMATION: synthetic DNA polymerase uracil-sensing domain
      (USD)

<400> SEQUENCE: 19

Ile Leu Asp Ala Asp Tyr Ile Thr Glu Glu Gly Lys Pro Val Ile Arg
 1               5                  10                  15

Leu Phe Lys Lys Glu Asn Gly Glu Phe Lys Ile Glu His Asp Arg Thr
            20                  25                  30

Phe Arg Pro Tyr Ile Tyr Ala Leu Leu Lys Asp Asp Ser Lys Ile Glu
        35                  40                  45

Glu Val Lys Lys Ile Thr Ala Glu Arg His Gly Lys Ile Val Arg Ile
    50                  55                  60

Val Asp Ala Glu Lys Val Glu Lys Lys Phe Leu Gly Arg Pro Ile Thr
65                  70                  75                  80

Val Trp Arg Leu Tyr Phe Glu His Pro Gln Asp Val Pro Thr Ile Arg
```

```
                85                  90                  95
Glu Lys Ile Arg Glu His Ser Ala Val Val Asp Ile Phe Glu Tyr Asp
            100                 105                 110

Ile Pro Phe Ala Lys Arg Tyr Leu Ile Asp Lys Gly Leu
            115                 120                 125

<210> SEQ ID NO 20
<211> LENGTH: 648
<212> TYPE: PRT
<213> ORGANISM: Artificial Sequence
<220> FEATURE:
<223> OTHER INFORMATION: synthetic Pfu/DeepVent hybrid DNA polymerase
      (polymerase portion)

<400> SEQUENCE: 20

Ile Pro Met Glu Gly Asp Glu Glu Leu Lys Leu Leu Ala Phe Ala Ile
1               5                   10                  15

Ala Thr Leu Tyr His Glu Gly Glu Phe Gly Lys Gly Pro Ile Ile
            20                  25                  30

Met Ile Ser Tyr Ala Asp Glu Glu Ala Lys Val Ile Thr Trp Lys
            35                  40                  45

Lys Ile Asp Leu Pro Tyr Val Glu Val Val Ser Ser Glu Arg Glu Met
50                  55                  60

Ile Lys Arg Phe Leu Lys Ile Ile Arg Glu Lys Asp Pro Asp Ile Ile
65                  70                  75                  80

Ile Thr Tyr Asn Gly Asp Ser Phe Asp Leu Pro Tyr Leu Ala Lys Arg
                85                  90                  95

Ala Glu Lys Leu Gly Ile Lys Leu Thr Ile Gly Arg Asp Gly Ser Glu
            100                 105                 110

Pro Lys Met Gln Arg Ile Gly Asp Met Thr Ala Val Glu Val Lys Gly
            115                 120                 125

Arg Ile His Phe Asp Leu Tyr His Val Ile Arg Arg Thr Ile Asn Leu
            130                 135                 140

Pro Thr Tyr Thr Leu Glu Ala Val Tyr Glu Ala Ile Phe Gly Lys Pro
145                 150                 155                 160

Lys Glu Lys Val Tyr Ala Asp Glu Ile Ala Lys Ala Trp Glu Thr Gly
                165                 170                 175

Glu Gly Leu Glu Arg Val Ala Lys Tyr Ser Met Glu Asp Ala Lys Ala
            180                 185                 190

Thr Tyr Glu Leu Gly Lys Glu Phe Phe Pro Met Glu Ala Gln Leu Ser
            195                 200                 205

Arg Leu Val Gly Gln Pro Leu Trp Asp Val Ser Arg Ser Ser Thr Gly
            210                 215                 220

Asn Leu Val Glu Trp Phe Leu Leu Arg Lys Ala Tyr Glu Arg Asn Glu
225                 230                 235                 240

Leu Ala Pro Asn Lys Pro Asp Glu Arg Glu Tyr Glu Arg Arg Leu Arg
                245                 250                 255

Glu Ser Tyr Ala Gly Gly Phe Val Lys Glu Pro Glu Lys Gly Leu Trp
            260                 265                 270

Glu Asn Ile Val Ser Leu Asp Phe Arg Ala Leu Tyr Pro Ser Ile Ile
            275                 280                 285

Ile Thr His Asn Val Ser Pro Asp Thr Leu Asn Arg Glu Gly Cys Arg
            290                 295                 300

Asn Tyr Asp Val Ala Pro Glu Val Gly His Lys Phe Cys Lys Asp Phe
305                 310                 315                 320
```

-continued

```
Pro Gly Phe Ile Pro Ser Leu Leu Lys Arg Leu Leu Asp Glu Arg Gln
                325                 330                 335

Lys Ile Lys Thr Lys Met Lys Ala Ser Gln Asp Pro Ile Glu Lys Ile
            340                 345                 350

Met Leu Asp Tyr Arg Gln Arg Ala Ile Lys Ile Leu Ala Asn Ser Tyr
        355                 360                 365

Tyr Gly Tyr Tyr Gly Tyr Ala Lys Ala Arg Trp Tyr Cys Lys Glu Cys
    370                 375                 380

Ala Glu Ser Val Thr Ala Trp Gly Arg Glu Tyr Ile Glu Phe Val Trp
385                 390                 395                 400

Lys Glu Leu Glu Glu Lys Phe Gly Phe Lys Val Leu Tyr Ile Asp Thr
                405                 410                 415

Asp Gly Leu Tyr Ala Thr Ile Pro Gly Gly Lys Ser Glu Glu Ile Lys
            420                 425                 430

Lys Lys Ala Leu Glu Phe Val Asp Tyr Ile Asn Ala Lys Leu Pro Gly
        435                 440                 445

Leu Leu Glu Leu Gly Tyr Glu Gly Phe Tyr Lys Arg Gly Phe Phe Val
    450                 455                 460

Thr Lys Lys Lys Tyr Ala Leu Ile Asp Glu Glu Gly Lys Ile Ile Thr
465                 470                 475                 480

Arg Gly Leu Glu Ile Val Arg Arg Asp Trp Ser Glu Ile Ala Lys Glu
                485                 490                 495

Thr Gln Ala Arg Val Leu Glu Ala Ile Leu Lys His Gly Asn Val Glu
            500                 505                 510

Glu Ala Val Arg Ile Val Lys Glu Val Thr Gln Lys Leu Ser Lys Tyr
        515                 520                 525

Glu Ile Pro Pro Glu Lys Leu Ala Ile Tyr Glu Gln Ile Thr Arg Pro
    530                 535                 540

Leu His Glu Tyr Lys Ala Ile Gly Pro His Val Ala Val Ala Lys Arg
545                 550                 555                 560

Leu Ala Ala Lys Gly Val Lys Ile Lys Pro Gly Met Val Ile Gly Tyr
                565                 570                 575

Ile Val Leu Arg Gly Asp Gly Pro Ile Ser Asn Arg Ala Ile Leu Ala
            580                 585                 590

Glu Glu Tyr Asp Pro Arg Lys His Lys Tyr Asp Ala Glu Tyr Tyr Ile
        595                 600                 605

Glu Asn Gln Val Leu Pro Ala Val Leu Arg Ile Leu Glu Gly Phe Gly
    610                 615                 620

Tyr Arg Lys Glu Asp Leu Arg Trp Gln Lys Thr Lys Gln Thr Gly Leu
625                 630                 635                 640

Thr Ser Trp Leu Asn Ile Lys Lys
                645

<210> SEQ ID NO 21
<211> LENGTH: 7
<212> TYPE: PRT
<213> ORGANISM: Artificial Sequence
<220> FEATURE:
<223> OTHER INFORMATION: synthetic linker between DNA polymerase portion
      and Sso7d

<400> SEQUENCE: 21

Ser Gly Thr Gly Gly Gly Gly
1               5

<210> SEQ ID NO 22
```

<211> LENGTH: 67
<212> TYPE: PRT
<213> ORGANISM: Artificial Sequence
<220> FEATURE:
<223> OTHER INFORMATION: synthetic Sso7d K28P mutant

<400> SEQUENCE: 22

Ala Thr Val Lys Phe Lys Tyr Lys Gly Glu Glu Lys Glu Val Asp Ile
1               5                   10                  15

Ser Lys Ile Lys Lys Val Trp Arg Val Gly Pro Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Ala Ala
    50                  55                  60

Ala Leu Glu
65

<210> SEQ ID NO 23
<211> LENGTH: 981
<212> TYPE: DNA
<213> ORGANISM: Artificial Sequence
<220> FEATURE:
<223> OTHER INFORMATION: synthetic codon-optimized Archaeon Pyrococcus
      furiosus flap endonuclease (Pfu FEN1) with
      C-terminal signal sequence and PCNA-interacting
      protein (PIP-box) motif deleted

<400> SEQUENCE: 23
atgggcgtgc cgatcggtga atcatccca cgtaaagaaa tcgagctgga gaacctgtac        60
ggtaaaaaaa ttgctatcga cgctctcaac gccatttacc agttcctgtc aactatccgt      120
cagaaagacg gcactccgct catggatagc aagggtcgta ttacctctca cctgtccggc      180
ctgttctacc gtacgatcaa tctgatggaa gcagggatta accggtcta tgtgttcgat       240 ggcgaaccgc cagagttcaa aaagaaagag ttggaaaaac gccgtgaagc acgtgaagaa      300
gcggaagaaa atggcgtga agctctggaa aaaggcgaaa tcgaagaagc gcgtaaatac      360
gcccagcgtg cgacccgtgt caatgaaatg ctgatcgaag acgccaaaaa actgctggaa      420
ttgatgggta tccctatcgt gcaggctcca tctgaaggcg aagctcaagc ggcgtatatg      480
gccgcaaaag gctctgttta tgcgtctgct tcccaagatt acgactccct gctgtttggt      540
gcaccgcgcc tggtgcgtaa cctgaccatc acgggtaagc gtaagttgcc gggtaagaac      600
gtttatgtgg aaattaaacc tgaactgatt attctggaag aggtcctgaa agagctgaaa      660
ctgacacgcg aaaaactgat tgaactggct atcctggttg gcacagacta acccaggc       720 ggtatcaaag gcatcggtct gaaaaaagcg cttgaaatcg tgcgtcacag taaagatccg      780
ctggctaagt tcagaaaca gagcgacgtg gacctgtatg caattaaaga gttcttcctg      840
aaccctccgg ttactgataa ctacaacctg gtttggcgcg atccagacga ggagggtatc      900
ctgaaatttc tgtgtgatga acacgatttc tccgaggaac gtgttaaaaa cggtctggag      960
cgtctgaaga aggcgatcaa a                                                 981

<210> SEQ ID NO 24
<211> LENGTH: 327
<212> TYPE: PRT
<213> ORGANISM: Artificial Sequence
<220> FEATURE:
<223> OTHER INFORMATION: synthetic codon-optimized Archaeon Pyrococcus
      furiosus flap endonuclease (Pfu FEN1) with
      C-terminal signal sequence and PCNA-interacting protein (PIP-box) motif deleted

<400> SEQUENCE: 24

Met Gly Val Pro Ile Gly Glu Ile Ile Pro Arg Lys Glu Ile Glu Leu
1               5                   10                  15

Glu Asn Leu Tyr Gly Lys Lys Ile Ala Ile Asp Ala Leu Asn Ala Ile
            20                  25                  30

Tyr Gln Phe Leu Ser Thr Ile Arg Gln Lys Asp Gly Thr Pro Leu Met
        35                  40                  45

Asp Ser Lys Gly Arg Ile Thr Ser His Leu Ser Gly Leu Phe Tyr Arg
    50                  55                  60

Thr Ile Asn Leu Met Glu Ala Gly Ile Lys Pro Val Tyr Val Phe Asp
65                  70                  75                  80

Gly Glu Pro Pro Glu Phe Lys Lys Glu Leu Glu Lys Arg Arg Glu
                85                  90                  95

Ala Arg Glu Glu Ala Glu Lys Trp Arg Glu Ala Leu Glu Lys Gly
                100                 105                 110

Glu Ile Glu Glu Ala Arg Lys Tyr Ala Gln Arg Ala Thr Arg Val Asn
            115                 120                 125

Glu Met Leu Ile Glu Asp Ala Lys Lys Leu Leu Glu Leu Met Gly Ile
    130                 135                 140

Pro Ile Val Gln Ala Pro Ser Glu Gly Glu Ala Gln Ala Ala Tyr Met
145                 150                 155                 160

Ala Ala Lys Gly Ser Val Tyr Ala Ser Ala Ser Gln Asp Tyr Asp Ser
                165                 170                 175

Leu Leu Phe Gly Ala Pro Arg Leu Val Arg Asn Leu Thr Ile Thr Gly
            180                 185                 190

Lys Arg Lys Leu Pro Gly Lys Asn Val Tyr Val Glu Ile Lys Pro Glu
        195                 200                 205

Leu Ile Ile Leu Glu Glu Val Leu Lys Glu Lys Leu Thr Arg Glu
    210                 215                 220

Lys Leu Ile Glu Leu Ala Ile Leu Val Gly Thr Asp Tyr Asn Pro Gly
225                 230                 235                 240

Gly Ile Lys Gly Ile Gly Leu Lys Lys Ala Leu Glu Ile Val Arg His
                245                 250                 255

Ser Lys Asp Pro Leu Ala Lys Phe Gln Lys Gln Ser Asp Val Asp Leu
            260                 265                 270

Tyr Ala Ile Lys Glu Phe Phe Leu Asn Pro Pro Val Thr Asp Asn Tyr
        275                 280                 285

Asn Leu Val Trp Arg Asp Pro Asp Glu Glu Gly Ile Leu Lys Phe Leu
    290                 295                 300

Cys Asp Glu His Asp Phe Ser Glu Glu Arg Val Lys Asn Gly Leu Glu
305                 310                 315                 320

Arg Leu Lys Lys Ala Ile Lys
                325

<210> SEQ ID NO 25
<211> LENGTH: 119
<212> TYPE: PRT
<213> ORGANISM: Artificial Sequence
<220> FEATURE:
<223> OTHER INFORMATION: synthetic Pfu/DeepVent hybrid DNA polymerase
      uracil-sensing domain (USD)

<400> SEQUENCE: 25

Ile Leu Asp Ala Asp Tyr Ile Thr Glu Glu Gly Lys Pro Val Ile Arg

```
                1               5                  10                  15
Leu Phe Lys Lys Glu Asn Gly Glu Phe Lys Ile Glu His Asp Arg Thr
                20                  25                  30

Phe Arg Pro Tyr Ile Tyr Ala Leu Leu Lys Asp Asp Ser Lys Ile Glu
            35                  40                  45

Glu Val Lys Lys Ile Thr Ala Glu Arg His Gly Lys Ile Val Arg Ile
    50                  55                  60

Val Asp Ala Glu Lys Val Glu Lys Phe Leu Gly Arg Pro Ile Thr
65                  70                  75                  80

Val Trp Arg Leu Tyr Phe Glu His Pro Gln Asp Val Pro Thr Ile Arg
                85                  90                  95

Glu Lys Ile Arg Glu His Ser Ala Val Val Asp Ile Phe Glu Tyr Asp
            100                 105                 110

Ile Pro Phe Ala Lys Arg Tyr
            115
```

<210> SEQ ID NO 26
<211> LENGTH: 6
<212> TYPE: PRT
<213> ORGANISM: Artificial Sequence
<220> FEATURE:
<223> OTHER INFORMATION: synthetic amino acids deleted from DNA
      polymerase in addition to uracil-sensing domain (USD)

<400> SEQUENCE: 26

```
Leu Ile Asp Lys Gly Leu
1               5
```

<210> SEQ ID NO 27
<211> LENGTH: 64
<212> TYPE: PRT
<213> ORGANISM: Sulfolobus acidocaldarius
<220> FEATURE:
<223> OTHER INFORMATION: DNA-binding protein Sso7d/Ssh7A/SsoP2

<400> SEQUENCE: 27

```
Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
    50                  55                  60
```

<210> SEQ ID NO 28
<211> LENGTH: 64
<212> TYPE: PRT
<213> ORGANISM: Sulfolobus shibatae
<220> FEATURE:
<223> OTHER INFORMATION: DNA-binding protein Ssh7b

<400> SEQUENCE: 28

```
Met Val Thr Val Lys Phe Lys Tyr Lys Gly Glu Glu Lys Glu Val Asp
1               5                   10                  15

Thr Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
```

<210> SEQ ID NO 29
<211> LENGTH: 66
<212> TYPE: PRT
<213> ORGANISM: Sulfolobus acidocaldarius
<220> FEATURE:
<223> OTHER INFORMATION: DNA-binding protein Sac7d

<400> SEQUENCE: 29

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 30
<211> LENGTH: 65
<212> TYPE: PRT
<213> ORGANISM: Sulfolobus acidocaldarius
<220> FEATURE:
<223> OTHER INFORMATION: Sulfolobus acidocaldarius strain DSM 639
      DNA-binding protein 7e, Sac7e

<400> SEQUENCE: 30

Met Ala Lys Val Arg Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Met Asp Met Leu Ala Arg Ala Glu Lys Lys
    50                  55                  60

Lys
65

<210> SEQ ID NO 31
<211> LENGTH: 64
<212> TYPE: PRT
<213> ORGANISM: Sulfolobus tokodaii
<220> FEATURE:
<223> OTHER INFORMATION: Sulfolobus tokodaii strain 7 DNA-binding
      protein 7e, Sto7e

<400> SEQUENCE: 31

Met Val Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Gln Met Leu Glu Lys Ser Gly Lys Lys
    50                  55                  60

<210> SEQ ID NO 32
<211> LENGTH: 3465

<212> TYPE: DNA
<213> ORGANISM: Artificial Sequence
<220> FEATURE:
<223> OTHER INFORMATION: synthetic pET29b-Taq 5'Exo-Linker-Pfu/DeepVent hybrid DNA polymerase-HisTag full construct

<400> SEQUENCE: 32

| | | | | | |
|---|---|---|---|---|---|
| atgttaccct | tgtttgaacc | aaaaggtcgc | gttttattag | tagatggcca | tcacttagcc | 60 |
| taccgtacat | ttcacgcatt | aaaaggactg | actacctctc | gtggcgaacc | cgtccaagct | 120 |
| gtttatggat | ttgctaaatc | attattaaaa | gccttaaaag | aagatggtga | tgccgttatt | 180 |
| gtagttttcg | atgcaaaagc | cccctcattt | cggcacgagg | cttatggtgg | ttacaaagct | 240 |
| ggtcgtgcac | cgacgcccga | agattttccg | cgccagttag | cccttatcaa | agaactcgta | 300 |
| gatttattag | gtctcgcacg | cttagaagtc | cccggctacg | aagcagatga | cgttctcgcc | 360 |
| agccttgcca | agaaagcaga | aaaagaagga | tatgaagtac | gcatcctgac | agccgacaaa | 420 |
| gacttatacc | aactcctttc | agatcgcatc | cacgttttac | atcccgaagg | ctacttaatt | 480 |
| acccctgcat | ggctgtggga | aaaatatgga | ttacgtccgg | atcaatgggc | cgattaccgt | 540 |
| gctttaaccg | gtgatgaatc | agataacctc | ccaggtgtta | agggattgg | agaaaaaact | 600 |
| gcccgtaaat | tgttagaaga | atggggctct | ttggaagcac | tgttaaaaaa | ccttgatcgt | 660 |
| ctcaaacctg | ccatccgcga | aaaaattctg | gcccacatgg | atgacttaaa | actgagctgg | 720 |
| gatctcgcta | aagttcgtac | cgacttacct | cttgaagttg | attttgcaaa | acgccgtgaa | 780 |
| cctgatcgtg | aacgccttcg | tgcatttctt | gaacgtctgg | aatttggctc | cttgttacat | 840 |
| gaatttggcc | tcttagaatc | aggcggtggt | agcggtggcg | gcggttctgg | cggtggtggc | 900 |
| agcatcctgg | atgctgacta | catcactgaa | gaaggcaaac | cggttatccg | tctgttcaaa | 960 |
| aaagagaacg | gcgaatttaa | gattgagcat | gatcgcacct | tcgtccata | catttacgct | 1020 |
| ctgctgaaag | atgattctaa | gattgaggaa | gttaaaaaaa | tcactgctga | gcgccatggc | 1080 |
| aagattgttc | gtatcgttga | tgcggaaaag | gtagaaaaga | aatttctggg | cagaccaatc | 1140 |
| accgtgtgga | gactgtattt | cgaacatcca | aagatgttc | cgactattcg | cgagaaaatt | 1200 |
| cgcgaacatt | ctgcagttgt | tgacatcttc | gaatacgata | ttccatttgc | aaagcgttac | 1260 |
| ctcatcgaca | aaggcctgat | accaatggag | ggcgatgaag | aactcaagct | cctggcgttc | 1320 |
| gctatagcaa | ccctctatca | cgaaggcgaa | gagtttggta | aagcccaat | tataatgatc | 1380 |
| agctatgcag | atgaagaaga | agcaaaggtg | attacttgga | aaaaaataga | tctcccatac | 1440 |
| gttgaggttg | tatcttccga | gcgcgagatg | attaagcgct | ttctcaaaat | tatccgcgag | 1500 |
| aaggatccgg | acattatcat | tacttataac | ggcgactctt | ttgacctccc | atatctggcg | 1560 |
| aaacgcgcag | aaaaactcgg | tattaaactg | actatcggcc | gtgatggttc | cgagccgaag | 1620 |
| atgcagcgta | tcggcgatat | gaccgctgta | gaagttaagg | gtcgtatcca | tttcgacctg | 1680 |
| tatcatgtaa | ttcgtcgtac | tattaacctc | ccgacttaca | ctctcgaggc | tgtatatgaa | 1740 |
| gcaattttg | gtaagccgaa | ggagaaggta | tacgccgatg | agattgcaaa | ggcgtgggaa | 1800 |
| accggtgagg | gcctcgagcg | tgttgcaaaa | tactccatgg | aagatgcaaa | ggcgacttat | 1860 |
| gaactcggca | agaattctt | cccaatgaa | gctcagctct | tcgcctggt | tggccaacca | 1920 |
| ctgtgggatg | tttctcgttc | ttccaccggt | aacctcgtag | agtggtttct | cctgcgcaaa | 1980 |
| gcgtacgaac | gcaacgaact | ggctccgaac | aagccagatg | aacgtgagta | tgaacgccgt | 2040 |
| ctccgcgagt | cttacgctgg | tggctttgtt | aaagagccag | aaaagggcct | ctgggaaaac | 2100 |
| atcgtgtccc | tcgattttcg | cgctctgtat | ccgtctatta | tcattaccca | caacgtgtct | 2160 |

```
ccggatactc tcaaccgcga gggctgcaga aactatgatg ttgctccgga agtaggccac    2220
aagttctgca aggacttccc gggctttatt ccgtctctcc tgaaacgtct gctcgatgaa    2280
cgccaaaaga ttaagactaa aatgaaggcg tcccaggatc cgattgaaaa aataatgctc    2340
gactatcgcc aaagagcgat taaaatcctc gcaaactctt attacggcta ttatggctat    2400
gcaaaagcac gctggtactg taaggagtgt gctgagtccg ttactgcttg ggtcgcgaa     2460 tacatcgagt tcgtgtggaa ggagctcgaa gaaaagtttg gctttaaagt tctctacatt    2520
gacactgatg gtctctatgc gactattccg ggtggtaagt ctgaggaaat taagaaaaag    2580
gctctagaat ttgtggatta cattaacgcg aagctcccgg gtctcctgga gctcgaatat    2640
gaaggctttt ataaacgcgg cttcttcgtt accaagaaga aatatgcgct gattgatgaa    2700
gaaggcaaaa ttattactcg tggtctcgag attgtgcgcc gtgattggag cgaaattgcg    2760
aaagaaactc aagctagagt tctcgaggct attctcaaac acggcaacgt tgaagaagct    2820
gtgagaattg taaagaagt aacccaaaag ctctctaaat atgaaattcc gccagagaag     2880
ctcgcgattt atgagcagat tactcgcccg ctgcatgagt ataaggcgat tggtccgcac    2940
gtggctgttg caaagagact ggctgctaaa ggcgtgaaaa ttaaaccggg tatggtaatt    3000
ggctacattg tactccgcgg cgatggtccg attagcaacc gtgcaattct agctgaggaa    3060
tacgatccga gaaagcacaa gtatgacgca gaatattaca ttgagaacca ggtgctcccg    3120
gcggtactcc gtattctgga gggttttggc taccgtaagg aagacctccg ctggcaaaag    3180
actaaacaga ctggcctcac ttcttggctc aacattaaaa aatccggtac cggcggtggc    3240
ggtgcaaccg taaagttcaa gtacaaaggc gaagaaaaag aggtagacat ctccaagatc    3300
aagaaagtat ggcgtgtggg cccaatgatc tccttcacct acgacgaggg cggtggcaag    3360
accggccgtg gtgcggtaag cgaaaaggac gcgccgaagg agctgctgca gatgctggag    3420
aagcagaaag cggccgcact cgagcaccac caccaccacc actga                   3465
```

<210> SEQ ID NO 33
<211> LENGTH: 1154
<212> TYPE: PRT
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag full construct

<400> SEQUENCE: 33

```
Met Leu Pro Leu Phe Glu Pro Lys Gly Arg Val Leu Leu Val Asp Gly
  1               5                  10                  15

His His Leu Ala Tyr Arg Thr Phe His Ala Leu Lys Gly Leu Thr Thr
             20                  25                  30

Ser Arg Gly Glu Pro Val Gln Ala Val Tyr Gly Phe Ala Lys Ser Leu
         35                  40                  45

Leu Lys Ala Leu Lys Glu Asp Gly Asp Ala Val Ile Val Val Phe Asp
     50                  55                  60

Ala Lys Ala Pro Ser Phe Arg His Glu Ala Tyr Gly Gly Tyr Lys Ala
 65                  70                  75                  80

Gly Arg Ala Pro Thr Pro Glu Asp Phe Pro Arg Gln Leu Ala Leu Ile
                 85                  90                  95

Lys Glu Leu Val Asp Leu Leu Gly Leu Ala Arg Leu Glu Val Pro Gly
            100                 105                 110

Tyr Glu Ala Asp Asp Val Leu Ala Ser Leu Ala Lys Lys Ala Glu Lys
        115                 120                 125
```

-continued

Glu Gly Tyr Glu Val Arg Ile Leu Thr Ala Asp Lys Asp Leu Tyr Gln
    130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Leu Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser Gly
        275                 280                 285

Gly Gly Ser Gly Gly Gly Ser Gly Gly Gly Ser Ile Leu Asp
    290                 295                 300

Ala Asp Tyr Ile Thr Glu Glu Gly Lys Pro Val Ile Arg Leu Phe Lys
305                 310                 315                 320

Lys Glu Asn Gly Glu Phe Lys Ile Glu His Asp Arg Thr Phe Arg Pro
                325                 330                 335

Tyr Ile Tyr Ala Leu Leu Lys Asp Asp Ser Lys Ile Glu Glu Val Lys
            340                 345                 350

Lys Ile Thr Ala Glu Arg His Gly Lys Ile Val Arg Ile Val Asp Ala
        355                 360                 365

Glu Lys Val Glu Lys Lys Phe Leu Gly Arg Pro Ile Thr Val Trp Arg
    370                 375                 380

Leu Tyr Phe Glu His Pro Gln Asp Val Pro Thr Ile Arg Glu Lys Ile
385                 390                 395                 400

Arg Glu His Ser Ala Val Val Asp Ile Phe Glu Tyr Asp Ile Pro Phe
                405                 410                 415

Ala Lys Arg Tyr Leu Ile Asp Lys Gly Leu Ile Pro Met Glu Gly Asp
            420                 425                 430

Glu Glu Leu Lys Leu Leu Ala Phe Ala Ile Ala Thr Leu Tyr His Glu
        435                 440                 445

Gly Glu Glu Phe Gly Lys Gly Pro Ile Ile Met Ile Ser Tyr Ala Asp
    450                 455                 460

Glu Glu Glu Ala Lys Val Ile Thr Trp Lys Lys Ile Asp Leu Pro Tyr
465                 470                 475                 480

Val Glu Val Val Ser Ser Glu Arg Glu Met Ile Lys Arg Phe Leu Lys
                485                 490                 495

Ile Ile Arg Glu Lys Asp Pro Asp Ile Ile Thr Tyr Asn Gly Asp
            500                 505                 510

Ser Phe Asp Leu Pro Tyr Leu Ala Lys Arg Ala Glu Lys Leu Gly Ile
        515                 520                 525

Lys Leu Thr Ile Gly Arg Asp Gly Ser Glu Pro Lys Met Gln Arg Ile
    530                 535                 540

```
Gly Asp Met Thr Ala Val Glu Val Lys Gly Arg Ile His Phe Asp Leu
545                 550                 555                 560

Tyr His Val Ile Arg Arg Thr Ile Asn Leu Pro Thr Tyr Thr Leu Glu
            565                 570                 575

Ala Val Tyr Glu Ala Ile Phe Gly Lys Pro Lys Glu Lys Val Tyr Ala
                580                 585                 590

Asp Glu Ile Ala Lys Ala Trp Glu Thr Gly Glu Gly Leu Glu Arg Val
            595                 600                 605

Ala Lys Tyr Ser Met Glu Asp Ala Lys Ala Thr Tyr Glu Leu Gly Lys
            610                 615                 620

Glu Phe Phe Pro Met Glu Ala Gln Leu Ser Arg Leu Val Gly Gln Pro
625                 630                 635                 640

Leu Trp Asp Val Ser Arg Ser Thr Gly Asn Leu Val Glu Trp Phe
                645                 650                 655

Leu Leu Arg Lys Ala Tyr Glu Arg Asn Glu Leu Ala Pro Asn Lys Pro
                660                 665                 670

Asp Glu Arg Glu Tyr Glu Arg Leu Arg Glu Ser Tyr Ala Gly Gly
                675                 680                 685

Phe Val Lys Glu Pro Glu Lys Gly Leu Trp Glu Asn Ile Val Ser Leu
690                 695                 700

Asp Phe Arg Ala Leu Tyr Pro Ser Ile Ile Ile Thr His Asn Val Ser
705                 710                 715                 720

Pro Asp Thr Leu Asn Arg Glu Gly Cys Arg Asn Tyr Asp Val Ala Pro
                725                 730                 735

Glu Val Gly His Lys Phe Cys Lys Asp Phe Pro Gly Phe Ile Pro Ser
                740                 745                 750

Leu Leu Lys Arg Leu Leu Asp Glu Arg Gln Lys Ile Lys Thr Lys Met
                755                 760                 765

Lys Ala Ser Gln Asp Pro Ile Glu Lys Ile Met Leu Asp Tyr Arg Gln
770                 775                 780

Arg Ala Ile Lys Ile Leu Ala Asn Ser Tyr Tyr Gly Tyr Tyr Gly Tyr
785                 790                 795                 800

Ala Lys Ala Arg Trp Tyr Cys Lys Glu Cys Ala Glu Ser Val Thr Ala
                805                 810                 815

Trp Gly Arg Glu Tyr Ile Glu Phe Val Trp Lys Glu Leu Glu Glu Lys
                820                 825                 830

Phe Gly Phe Lys Val Leu Tyr Ile Asp Thr Asp Gly Leu Tyr Ala Thr
            835                 840                 845

Ile Pro Gly Gly Lys Ser Glu Glu Ile Lys Lys Ala Leu Glu Phe
850                 855                 860

Val Asp Tyr Ile Asn Ala Lys Leu Pro Gly Leu Leu Glu Leu Glu Tyr
865                 870                 875                 880

Glu Gly Phe Tyr Lys Arg Gly Phe Phe Val Thr Lys Lys Lys Tyr Ala
                885                 890                 895

Leu Ile Asp Glu Glu Gly Lys Ile Ile Thr Arg Gly Leu Glu Ile Val
            900                 905                 910

Arg Arg Asp Trp Ser Glu Ile Ala Lys Glu Thr Gln Ala Arg Val Leu
            915                 920                 925

Glu Ala Ile Leu Lys His Gly Asn Val Glu Glu Ala Val Arg Ile Val
            930                 935                 940

Lys Glu Val Thr Gln Lys Leu Ser Lys Tyr Glu Ile Pro Pro Glu Lys
945                 950                 955                 960

Leu Ala Ile Tyr Glu Gln Ile Thr Arg Pro Leu His Glu Tyr Lys Ala
```

```
                965                 970                 975
Ile Gly Pro His Val Ala Val Ala Lys Arg Leu Ala Ala Lys Gly Val
            980                 985                 990

Lys Ile Lys Pro Gly Met Val Ile Gly Tyr Ile Val Leu Arg Gly Asp
        995                1000                1005

Gly Pro Ile Ser Asn Arg Ala Ile Leu Ala Glu Glu Tyr Asp Pro Arg
       1010                1015                1020

Lys His Lys Tyr Asp Ala Glu Tyr Tyr Ile Glu Asn Gln Val Leu Pro
1025                1030                1035                1040

Ala Val Leu Arg Ile Leu Glu Gly Phe Gly Tyr Arg Lys Glu Asp Leu
            1045                1050                1055

Arg Trp Gln Lys Thr Lys Gln Thr Gly Leu Thr Ser Trp Leu Asn Ile
       1060                1065                1070

Lys Lys Ser Gly Thr Gly Gly Gly Ala Thr Val Lys Phe Lys Tyr
       1075                1080                1085

Lys Gly Glu Glu Lys Glu Val Asp Ile Ser Lys Ile Lys Lys Val Trp
       1090                1095                1100

Arg Val Gly Pro Met Ile Ser Phe Thr Tyr Asp Glu Gly Gly Gly Lys
1105                1110                1115                1120

Thr Gly Arg Gly Ala Val Ser Glu Lys Asp Ala Pro Lys Glu Leu Leu
            1125                1130                1135

Gln Met Leu Glu Lys Gln Lys Ala Ala Ala Leu Glu His His His His
            1140                1145                1150

His His
```

<210> SEQ ID NO 34
<211> LENGTH: 861
<212> TYPE: DNA
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag codon-optimized Taq 5'Exo domain

<400> SEQUENCE: 34

```
atgttaccct tgtttgaacc aaaaggtcgc gttttattag tagatggcca tcacttagcc    60
taccgtacat ttcacgcatt aaaaggactg actacctctc gtggcgaacc cgtccaagct   120
gtttatggat ttgctaaatc attattaaaa gccttaaaag aagatggtga tgccgttatt   180
gtagttttcg atgcaaaagc cccctcattt cggcacgagg cttatggtgg ttacaaagct   240
ggtcgtgcac cgacgcccga gattttccgc gccagttag cccttatcaa gaactcgta    300
gatttattag gtctcgcacg cttagaagtc cccggctacg aagcagatga cgttctcgcc   360
agccttgcca gaaagcaga aaagaagga tatgaagtac gcatcctgac agccgacaaa    420
gacttatacc aactcctttc agatcgcatc cacgtttac atcccgaagg ctacttaatt    480
accccctgcat ggctgtggga aaaatatgga ttacgtccgg atcaatgggc cgattaccgt   540
gctttaaccg gtgatgaatc agataacctg ccaggtgtta agggattgg agaaaaaact   600
gcccgtaaat tgttagaaga atggggctct ttggaagcac tgttaaaaaa ccttgatcgt   660
ctcaaacctg ccatccgcga aaaattctg gcccacatgg atgacttaaa actgagctgg   720
gatctcgcta aagttcgtac cgacttacct cttgaagttg attttgcaaa cgccgtgaa    780
cctgatcgtg aacgccttcg tgcatttctt gaacgtctgg aatttggctc cttgttacat   840
gaatttggcc tcttagaatc a                                              861
```

-continued

```
<210> SEQ ID NO 35
<211> LENGTH: 287
<212> TYPE: PRT
<213> ORGANISM: Artificial Sequence
<220> FEATURE:
<223> OTHER INFORMATION: synthetic pET29b-Taq 5'Exo-Linker-Pfu/DeepVent
      hybrid DNA polymerase-HisTag Taq 5'Exo domain

<400> SEQUENCE: 35
```

Met Leu Pro Leu Phe Glu Pro Lys Gly Arg Val Leu Leu Val Asp Gly
 1               5                  10                  15

His His Leu Ala Tyr Arg Thr Phe His Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Asp Ala Val Ile Val Val Phe Asp
    50                  55                  60

Ala Lys Ala Pro Ser Phe Arg His Glu Ala Tyr Gly Gly Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Ala Arg Leu Glu Val Pro Gly
            100                 105                 110

Tyr Glu Ala Asp Asp Val Leu Ala Ser Leu Ala Lys Lys Ala Glu Lys
        115                 120                 125

Glu Gly Tyr Glu Val Arg Ile Leu Thr Ala Asp Lys Asp Leu Tyr Gln
    130                 135                 140

Leu Leu Ser Asp Arg Ile His Val Leu His Pro Glu Gly Tyr Leu Ile
145                 150                 155                 160

Thr Pro Ala Trp Leu Trp Glu Lys Tyr Gly Leu Arg Pro Asp Gln Trp
                165                 170                 175

Ala Asp Tyr Arg Ala Leu Thr Gly Asp Glu Ser Asp Asn Leu Pro Gly
            180                 185                 190

Val Lys Gly Ile Gly Glu Lys Thr Ala Arg Lys Leu Leu Glu Glu Trp
        195                 200                 205

Gly Ser Leu Glu Ala Leu Leu Lys Asn Leu Asp Arg Leu Lys Pro Ala
    210                 215                 220

Ile Arg Glu Lys Ile Leu Ala His Met Asp Asp Leu Lys Leu Ser Trp
225                 230                 235                 240

Asp Leu Ala Lys Val Arg Thr Asp Leu Pro Leu Glu Val Asp Phe Ala
                245                 250                 255

Lys Arg Arg Glu Pro Asp Arg Glu Arg Leu Arg Ala Phe Leu Glu Arg
            260                 265                 270

Leu Glu Phe Gly Ser Leu Leu His Glu Phe Gly Leu Leu Glu Ser
        275                 280                 285

```
<210> SEQ ID NO 36
<211> LENGTH: 42
<212> TYPE: DNA
<213> ORGANISM: Artificial Sequence
<220> FEATURE:
<223> OTHER INFORMATION: synthetic linker bbetween Taq 5'Exo domain and
      Pfu/DeepVent hybrid DNA polymerase

<400> SEQUENCE: 36
ggcggtggta gcggtggcgg cggttctggc ggtggtggca gc                           42

<210> SEQ ID NO 37
```

```
<211> LENGTH: 14
<212> TYPE: PRT
<213> ORGANISM: Artificial Sequence
<220> FEATURE:
<223> OTHER INFORMATION: synthetic linker between Taq 5'Exo domain and
      Pfu/DeepVent hybrid DNA polymerase

<400> SEQUENCE: 37

Gly Gly Gly Ser Gly Gly Gly Ser Gly Gly Gly Ser
1               5                   10

<210> SEQ ID NO 38
<211> LENGTH: 119
<212> TYPE: PRT
<213> ORGANISM: Artificial Sequence
<220> FEATURE:
<223> OTHER INFORMATION: synthetic Archaeon Pyrococcus furiosus (Pfu)
      DNA polymerase uracil-sensing domain (USD)

<400> SEQUENCE: 38

Ile Leu Asp Val Asp Tyr Ile Thr Glu Glu Gly Lys Pro Val Ile Arg
1               5                   10                  15

Leu Phe Lys Lys Glu Asn Gly Lys Phe Lys Ile Glu His Asp Arg Thr
            20                  25                  30

Phe Arg Pro Tyr Ile Tyr Ala Leu Leu Arg Asp Asp Ser Lys Ile Glu
        35                  40                  45

Glu Val Lys Lys Ile Thr Gly Glu Arg His Gly Lys Ile Val Arg Ile
    50                  55                  60

Val Asp Val Glu Lys Val Glu Lys Lys Phe Leu Gly Lys Pro Ile Thr
65                  70                  75                  80

Val Trp Lys Leu Tyr Leu Glu His Pro Gln Asp Val Pro Thr Ile Arg
                85                  90                  95

Glu Lys Val Arg Glu His Pro Ala Val Val Asp Ile Phe Glu Tyr Asp
            100                 105                 110

Ile Pro Phe Ala Lys Arg Tyr
        115

<210> SEQ ID NO 39
<211> LENGTH: 6
<212> TYPE: PRT
<213> ORGANISM: Artificial Sequence
<220> FEATURE:
<223> OTHER INFORMATION: synthetic 6-His epitope tag

<400> SEQUENCE: 39

His His His His His His
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic anti-DYKDDDDK epitope tag

<400> SEQUENCE: 40

Asp Tyr Lys Asp Asp Asp Asp Lys
1               5

<210> SEQ ID NO 41
<211> LENGTH: 4
<212> TYPE: PRT
<213> ORGANISM: Artificial Sequence
<220> FEATURE:
```

-continued

<223> OTHER INFORMATION: synthetic DNA-dependent DNA polymerase II
      family B region of similarity I conserved tetrapeptide motif

<400> SEQUENCE: 41

Asp Thr Asp Ser
1